(12) United States Patent
Hsiao

(10) Patent No.: US 10,471,064 B2
(45) Date of Patent: Nov. 12, 2019

(54) MEDICAMENT FOR TREATING PERIPHERAL NEUROPATHIES

(71) Applicant: Lily Hsiao, Nantou County (TW)

(72) Inventor: Lily Hsiao, Nantou County (TW)

(73) Assignee: Lily Hsiao, Nantou (TW)

( * ) Notice: Subject to any disclaimer, the term of this patent is extended or adjusted under 35 U.S.C. 154(b) by 77 days.

(21) Appl. No.: 15/915,040

(22) Filed: Mar. 7, 2018

(65) Prior Publication Data

US 2018/0193348 A1 Jul. 12, 2018

Related U.S. Application Data

(63) Continuation-in-part of application No. 13/752,403, filed on Jan. 29, 2013, now abandoned.

(51) Int. Cl.
| | | |
|---|---|---|
| *A61K 31/52* | (2006.01) | |
| *A61K 31/137* | (2006.01) | |
| *A61K 31/138* | (2006.01) | |
| *A61K 31/522* | (2006.01) | |
| *A61P 31/22* | (2006.01) | |
| *A61K 31/445* | (2006.01) | |
| *A61K 31/55* | (2006.01) | |
| *A61K 31/235* | (2006.01) | |
| *A61K 31/4545* | (2006.01) | |
| *A61K 31/495* | (2006.01) | |
| *A61K 31/335* | (2006.01) | |
| *A61K 31/5415* | (2006.01) | |

(52) U.S. Cl.
CPC .......... *A61K 31/522* (2013.01); *A61K 31/235* (2013.01); *A61K 31/335* (2013.01); *A61K 31/445* (2013.01); *A61K 31/4545* (2013.01); *A61K 31/495* (2013.01); *A61K 31/5415* (2013.01); *A61K 31/55* (2013.01); *A61P 31/22* (2018.01)

(58) Field of Classification Search
CPC .... A61K 31/52; A61K 31/137; A61K 31/138; A61K 31/252
USPC ............................ 514/263.34, 529, 659, 662
See application file for complete search history.

(56) References Cited

U.S. PATENT DOCUMENTS

| | | | | |
|---|---|---|---|---|
| 8,729,058 B2* | 5/2014 | Zasloff | .................. | A61K 31/56 514/182 |
| 2005/0014729 A1* | 1/2005 | Pulaski | .................. | A61K 31/00 514/165 |
| 2012/0093738 A1* | 4/2012 | Pilgaonkar | ........... | A61K 9/0056 424/44 |
| 2013/0059019 A1* | 3/2013 | Leighton | .............. | A61K 9/0014 424/736 |

* cited by examiner

*Primary Examiner* — Raymond J Henley, III
(74) *Attorney, Agent, or Firm* — Min-Lee Teng; Litron Patent and Trademark Office

(57) ABSTRACT

The invention provides a pharmaceutical composition for treating atopic dermatitis of a human that is induced by Herpes simplex virus (HSV), said pharmaceutical composition comprising an effective amount of 2-[(2-amino-6-oxo-6,9-dihydro-3H-purin-9-yl)methoxy]ethyl-2-amino-3-methylbutanoate and an effective amount of an Anti-allergic agent.

9 Claims, 59 Drawing Sheets

MEDICAMENT FOR TREATING PERIPHERAL NEUROPATHIES

CROSS REFERENCE TO RELATED APPLICATIONS

This application is a continuation in part of U.S. application Ser. No. 13/752,403, filed on Jan. 29, 2013, now abandoned, which is incorporated by reference herein in their entirety.

BACKGROUND OF THE INVENTION

1. Field of the Invention

The present invention relates generally to the diagnosis and treatment of the HSV (herpes simplex virus) infection of the dermal nerve fibers (DNFs) and free nerve endings (FNEs) in the skin.

2. Description of the Prior Art

Herpes simplex virus (HSV) is distributed worldwide, with humans being the only natural reservoirs. The most important biologic property of HSV is its capacity to invade and replicate in the nervous system, and this may cause life-threatening complications. HSV establishes and maintains a latent infection in the nerve ganglion proximal to the site of primary infection. In or facial HSV infection, the trigeminal ganglia are most commonly affected. In genital HSV infection, the sacral nerve root ganglia (S2-S5) are involved. Reactivation of the established latent infection can be induced by various stimuli (e.g., fever, trauma, emotional stress, sunlight, and menstruation) resulting in overt or covert recurrent infection. These unique biologic properties of latent infection and periodic reactivation, along with asymptomatic virus shedding, enable HSV endemicity to be maintained easily in most human communities.

SUMMARY OF THE INVENTION

According to one embodiment, the invention provides a method for a treatment of the diseases in a human by identifying the human as one suffering from a herpes simplex virus (HSV), and then administering to the human a compound anti-HSV agent or a pharmaceutically acceptable salt thereof.

According to one embodiment, the invention provides a method for treating acne in a human, comprising administering to said human an anti-Herpes simplex virus (HSV) agent.

According to another embodiment, the invention provides a method for treating acne in a human, comprising identifying said human as one suffering from herpes simplex viruses (HSV), and then administering to said human an anti-HSV agent or a pharmaceutically acceptable salt thereof.

According to another embodiment, the invention provides a method for treating acne in a human, comprising positively finding balloon cells and multinucleated giant cells containing intranuclear eosinophilic inclusion bodies from a pathological specimen removed from said human by using a stain solution, and then administering to the human an anti-Herpes simplex virus (HSV) agent or a pharmaceutically acceptable salt thereof.

According to another embodiment, the invention provides a method for treating impetigo in a human, comprising administering to said human an anti-Herpes simplex virus (HSV) agent.

According to another embodiment, the invention provides a method for treating impetigo in a human, comprising identifying said human as one suffering from herpes simplex viruses (HSV), and then administering to said human an anti-HSV agent or a pharmaceutically acceptable salt thereof.

According to another embodiment, the invention provides a method for treating impetigo in a human, comprising positively finding balloon cells and multinucleated giant cells containing intranuclear eosinophilic inclusion bodies from a pathological specimen removed from said human by using a stain solution, and then administering to the human an anti-Herpes simplex virus (HSV) agent or a pharmaceutically acceptable salt thereof.

According to another embodiment, the invention provides a method for treating pyoderma gangrenosum in a human, comprising administering to said human an anti-Herpes simplex virus (HSV) agent.

According to another embodiment, the invention provides a method for treating pyoderma gangrenosum in a human, comprising identifying said human as one suffering from herpes simplex viruses (HSV), and then administering to said human an anti-HSV agent or a pharmaceutically acceptable salt thereof.

According to another embodiment, the invention provides a method for treating pyoderma gangrenosum in a human, comprising positively finding balloon cells and multinucleated giant cells containing intranuclear eosinophilic inclusion bodies from a pathological specimen removed from said human by using a stain solution, and then administering to the human an anti-Herpes simplex virus (HSV) agent or a pharmaceutically acceptable salt thereof.

According to another embodiment, the invention provides a method for treating chilblain in a human, comprising administering to said human an anti-Herpes simplex virus (HSV) agent.

According to another embodiment, the invention provides a method for treating chilblain in a human, comprising identifying said human as one suffering from herpes simplex viruses (HSV), and then administering to said human an anti-HSV agent or a pharmaceutically acceptable salt thereof.

According to another embodiment, the invention provides a method for treating chilblain in a human, comprising positively finding balloon cells and multinucleated giant cells containing intranuclear eosinophilic inclusion bodies from a pathological specimen removed from said human by using a stain solution, and then administering to the human an anti-Herpes simplex virus (HSV) agent or a pharmaceutically acceptable salt thereof.

According to another embodiment, the invention provides a method for treating diabetic skin complications in a human, comprising administering to said human an anti-Herpes simplex virus (HSV) agent.

According to another embodiment, the invention provides a method for treating diabetic skin complications in a human, comprising identifying said human as one suffering from herpes simplex viruses (HSV), and then administering to said human an anti-HSV agent or a pharmaceutically acceptable salt thereof.

According to another embodiment, the invention provides a method for treating diabetic skin complications in a human, comprising positively finding balloon cells and multinucleated giant cells containing intranuclear eosinophilic inclusion bodies from a pathological specimen removed from said human by using a stain solution, and then administering to the human an anti-Herpes simplex virus (HSV) agent or a pharmaceutically acceptable salt thereof.

These and other objectives of the present invention will no doubt become obvious to those of ordinary skill in the art after reading the following detailed description of the preferred embodiment that is illustrated in the various figures and drawings.

According to one embodiment, the invention provides a method for treating alopecia in a human, comprising administering to said human an anti-Herpes simplex virus (HSV) agent.

According to another embodiment, the invention provides a method for treating alopecia in a human, comprising identifying said human as one suffering from herpes simplex viruses (HSV), and then administering to said human an anti-HSV agent or a pharmaceutically acceptable salt thereof.

According to another embodiment, the invention provides a method for treating alopecia in a human, comprising positively finding balloon cells and multinucleated giant cells containing intranuclear eosinophilic inclusion bodies from a pathological specimen removed from said human by using a stain solution, and then administering to the human an anti-Herpes simplex virus (HSV) agent or a pharmaceutically acceptable salt thereof.

DETAILED DESCRIPTION

Figure 1:
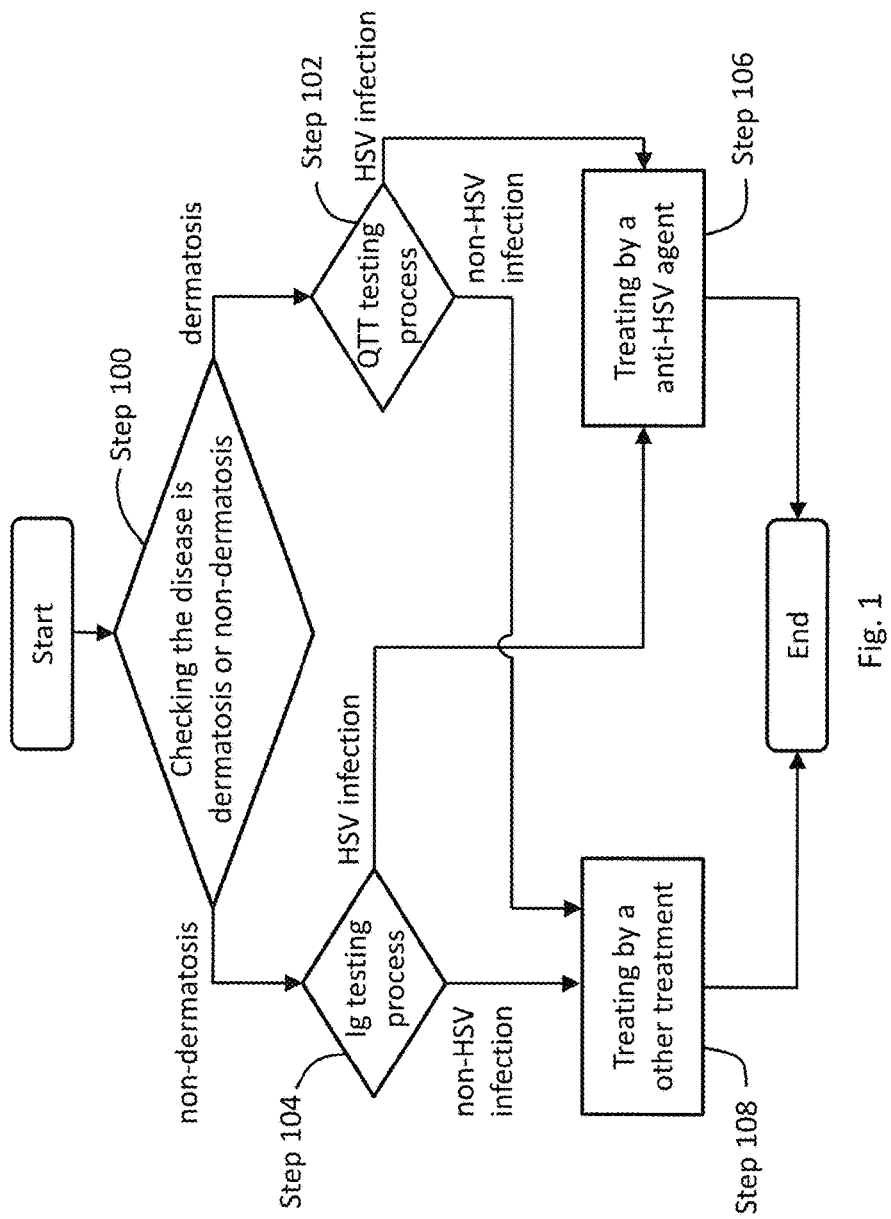
FIG. 1 is a flow chart of the detecting method in the present invention.

The invention provides a method for treatment of the diseases in a human by identifying the human as one suffering from a herpes simplex virus (HSV), and then administering to the human an anti-HSV agent or the combination thereof or a pharmaceutically acceptable salt thereof.

The diseases can be dermatosis or non-dermatosis, wherein the dermatosis include acne, impetigo, pyoderma gangrenosum, chilblains and psoriasiform, asteatotic dermatitis, ichthyosis, lichen simplex chronicus (neurodermatitis, prurigo), seborrhoeic dermatitis, rosacea, perioral dermatitis, epidermal cyst, wound ulcer, discoid lupus erythematosus, vitiligo, alopecia, diagnostic criteria of some autoimmune diseases such as systemic lupus erythematosus and diabetic skin complications. The non-dermatosis include glomerulonephritis, arthritis, Crohn's disease, ulcerative colitis, myelodysplasia, multiple myeloma, demyelinating disease, Parkinson's disease, and anemia, cytopenia those among the diagnostic criteria.

The following sequence commentary a cause, a signs and a symptom of the disease.

Acne: Acne develops as a result of blockages in the follicles. Hyperkeratinization and formation of a plug of keratin and sebum (a microcomedo) is the earliest change. Enlargement of sebaceous glands and an increase in sebum production occur with increased androgen (DHEA-S) production at adrenarche. The microcomedo may enlarge to form an open comedone (blackhead) or closed comedone (milia). Comedones are the direct result of sebaceous glands becoming clogged with sebum, a naturally occurring oil, and dead skin cells.

Impetigo: Impetigo is a highly contagious bacterial skin infection most common among pre-school children. This common form of impetigo, also called non-bullous impetigo, most often begins as a red sore near the nose or mouth which soon breaks, leaking pus or fluid, and forms a honey-colored scab followed by a red mark which heals without leaving a scar. Sores are not painful but may be itchy. Lymph nodes in the affected area may be swollen, but fever is rare. Touching or scratching the sores may easily spread the infection to other parts of the body.

Pyoderma gangrenosum: Pyoderma gangrenosum is a condition that causes tissue to become necrotic, causing deep ulcers that usually occur on the legs. When they occur, they can lead to chronic wounds. Ulcers usually initially look like small bug bites or papules, and they progress to larger ulcers. Though the etiology is not well understood, the disease is thought to be due to immune system dysfunction, and particularly improper functioning of neutrophils. At least half of all pyoderma gangrenosum patients also suffer from illnesses that affect their systemic function. For instance, ulcerative colitis, rheumatoid arthritis, and multiple myeloma sufferers have the condition.

Chilblains: Chilblain is a tissue injury that occurs when a predisposed individual is exposed to cold and humidity. The cold exposure damages capillary beds in the skin, which in turn can cause redness, itching, blisters, and inflammation. The areas most affected are the ears, earlobes, nose, and extremities; feet and toes, hands and fingers.

Psoriasiform: Psoriasiform is typically found in rheumatoid arthritis, crohn's disease, high blood pressure, psoriasis, ankylosing spondylitis. Psoriasis is a condition of the skin, which develop skin rashes and the skin at these particular areas is red, itchy and flaky. The psoriasis is not contagious. The researchers have found (so far) that psoriasis is caused by psychological factors such as too much stress.

Asteatotic dermatitis: Asteatotic dermatitis is a form of eczema that is characterized by changes that occur when skin becomes abnormally dry, itchy, and cracked. Lower legs tend to be especially affected, although it can appear in the underarm area as well. The asteatotic dermatitis is common in elderly people, though it is not uncommon for people in their 20s. It can appear in red, bumpy, pimple-like irritations.

Ichthyosis: All types of ichthyosis have dry, thickened, scaly or flaky skin. There are many types of ichthyosis and an exact diagnosis may be difficult. Types of ichthyosis are classified by their appearance and their genetic cause. Ichthyosis caused by the same gene can vary considerably in severity and symptoms.

Lichen Simplex Chronicus: Lichen simplex chronicus (also known as "Neurodermatitis") is a skin disorder characterized by chronic itching and scratching. The constant scratching causes thick, leathery, brownish skin.

Seborrhoeic dermatitis: Seborrhoeic dermatitis is an inflammatory skin disorder affecting the scalp, face, and torso. Typically, seborrheic dermatitis presents with scaly, flaky, itchy, and red skin. It particularly affects the sebaceous-gland-rich areas of skin. In adolescents and adults, seborrhoeic dermatitis usually presents as scalp scaling similar to dandruff or as mild to marked erythema of the nasolabial fold.

Rosacea: Rosacea is a chronic condition characterized by facial erythema (redness) and sometimes pimples. Rosacea affects adults and has four subtypes. Left untreated it worsens over time. Triggers that cause episodes of flushing and blushing play a part in the development of rosacea. Exposure to temperature extremes can cause the face to become flushed as well as strenuous exercise, heat from sunlight, severe sunburn, stress, anxiety, cold wind, and moving to a warm or hot environment from a cold one such as heated shops and offices during the winter.

Perioral dermatitis: Perioral dermatitis, a condition related to acne vulgaris, consists of red papules that may appear microvesicular that typically affect the nasolabial folds (around the nostrils), perioral area (around the mouth) or perioccular area (around the eyes).

Epidermal cyst: Epidermal cyst is a benign cyst usually found on the skin. The cyst develops out of ectodermal tissue. Histologically, it is made of a thin layer of squamous epithelium.

Wound ulcer: An ulcer is a sore on the skin or a mucous membrane, accompanied by the disintegration of tissue. Ulcers can result in complete loss of the epidermis and often portions of the dermis and even subcutaneous fat. Ulcers are most common on the skin of the lower extremities and in the gastrointestinal tract. An ulcer that appears on the skin is often visible as an inflamed tissue with an area of reddened skin. Ulcers often become infected, and pus forms.

Discoid lupus erythematosus (DLE): DLE is a chronic skin condition of sores with inflammation and scarring favoring the face, ears, and scalp and at times on other body areas. These lesions develop as a red, inflamed patch with a scaling and crusty appearance.

Vitiligo: Vitiligo is a condition that causes depigmentation of sections of skin. It occurs when melanocytes, the cells responsible for skin pigmentation, die or are unable to function. The cause of vitiligo is unknown, but research suggests that it may arise from autoimmune, genetic, oxidative stress, neural, or viral causes. The incidence worldwide is less than 1%. The most common form is non-segmental vitiligo, which tends to appear in symmetric patches, sometimes over large areas of the body.

Alopecia: Alopecia means loss of hair from the head or body. Alopecia can mean baldness, a term generally reserved for pattern alopecia or androgenic alopecia.

Diabetic skin complications: The diabetes patient need to be aware of potentially serious skin problems related to the disease. In most cases, skin problems in diabetes can be managed with early diagnosis and treatment. The diabetic skin complications comprising:

*Scleroderma diabeticorum*: While rare, this skin problem affects people with type 2 diabetes, causing a thickening of the skin on the back of the neck and upper back.

Vitiligo, a skin problem more commonly associated with type 1 diabetes than type 2 diabetes, affects skin coloration.

*Acanthosis nigricans*: This is a skin problem that results in the darkening and thickening of certain areas of the skin especially in the skin folds. The skin becomes tan or brown and is sometimes slightly raised and described as velvety. *Acanthosis nigricans* usually strikes people who are very overweight. While there is no cure for *acanthosis nigricans*, losing weight may improve the skin condition. *Acanthosis nigricans* usually precedes diabetes and is considered to be a marker for the disease.

Diabetic blisters (bullosis diabeticorum): In rare cases, people with diabetes develop skin problems, such as blisters that resemble burn blisters. These blisters can occur on the fingers, hands, toes, feet, legs, or forearms. Diabetic blisters usually are painless and heal on their own. These skin problems often occur in people who have severe diabetes and diabetic neuropathy.

Glomerulonephritis: Glomerulonephritis (GN) is a renal disease characterized by inflammation of the glomeruli, or small blood vessels in the kidneys. It may present with isolated hematuria and/or proteinuria (blood or protein in the urine); or as a nephrotic syndrome, a nephritic syndrome, acute renal failure, or chronic renal failure. They are categorized into several different pathological patterns, which are broadly grouped into non-proliferative or proliferative types. Diagnosing the pattern of GN is important because the outcome and treatment differs in different types. Primary causes are intrinsic to the kidney. Secondary causes are associated with certain infections (bacterial, viral or parasitic pathogens), drugs, systemic disorders (SLE, vasculitis), or diabetes.

Arthritis: Arthritis is a form of joint disorder that involves inflammation of one or more joints. There are over 100 different forms of arthritis. The most common form, osteoarthritis (degenerative joint disease), is a result of trauma to the joint, infection of the joint, or age. Other arthritis forms are rheumatoid arthritis, psoriatic arthritis, and related autoimmune diseases. Septic arthritis is caused by joint infection. The major complaint by individuals who have arthritis is joint pain. Pain is often a constant and may be localized to the joint affected. The pain from arthritis is due to inflammation that occurs around the joint, damage to the joint from disease, daily wear and tear of joint, muscle strains caused by forceful movements against stiff painful joints and fatigue.

Crohn's disease: Crohn's disease is a type of inflammatory bowel disease that may affect any part of the gastrointestinal tract from mouth to anus, causing a wide variety of symptoms. It primarily causes abdominal pain, diarrhea (which may be bloody if inflammation is at its worst), vomiting (can be continuous), or weight loss, but may also cause complications outside the gastrointestinal tract such as skin rashes, arthritis, inflammation of the eye, tiredness, and lack of concentration. Crohn's disease is caused by interactions between environmental, immunological and bacterial factors in genetically susceptible individuals. This result in a chronic inflammatory disorder, in which the body's immune system attacks the gastrointestinal tract possibly directed at microbial antigens. Crohn's disease has traditionally been described as an autoimmune disease, but recent investigators have described it as an immune deficiency state.

Myelodysplasia: The myelodysplastic syndromes (MDS, formerly known as preleukemia) are a diverse collection of hematological (blood-related) medical conditions that involve ineffective production (or dysplasia) of the myeloid class of blood cells. Patients with MDS often develop severe anemia and require frequent blood transfusions. In most cases, the disease worsens and the patient develops cytopenias (low blood counts) caused by progressive bone marrow failure. In about one third of patients with MDS, the disease transforms into acute myelogenous leukemia (AML), usually within months to a few years.

Multiple myeloma: Multiple myeloma is a cancer of plasma cells, a type of white blood cell normally responsible for producing antibodies. In multiple myeloma, collections of abnormal plasma cells accumulate in the bone marrow, where they interfere with the production of normal blood cells. Most cases of myeloma also feature the production of a paraprotein an abnormal antibody which can cause kidney problems. Bone lesions and hypercalcemia (high calcium levels) are also often encountered. Myeloma is generally thought to be treatable but incurable. Remissions may be induced with steroids, chemotherapy, proteasome inhibitors (e.g. bortezomib), immunomodulatory drugs (IMiDs) such as thalidomide or lenalidomide, and stem cell transplants. Radiation therapy is sometimes used to reduce pain from bone lesions.

Demyelinating disease: Demyelinating disease is any disease of the nervous system in which the myelin sheath of neurons is damaged. This impairs the conduction of signals in the affected nerves, causing impairment in sensation, movement, cognition, or other functions depending on which nerves are involved. Some demyelinating diseases are caused by genetics, some by infectious agents, some by autoimmune reactions, and some by unknown factors.

Anemia: Anemia is a decrease in number of red blood cells (RBCs) or less than the normal quantity of hemoglobin in the blood. However, it can include decreased oxygen-binding ability of each hemoglobin molecule due to deformity or lack in numerical development as in some other types of hemoglobin deficiency. Because hemoglobin normally carries oxygen from the lungs to the capillaries, anemia leads to hypoxia (lack of oxygen) in organs.

Ulcerative colitis: Ulcerative colitis (Colitis ulcerosa, UC) is a form of inflammatory bowel disease (IBD). Ulcerative colitis is a form of colitis, a disease of the colon (large intestine) that includes characteristic ulcers, or open sores. The main symptom of active disease is usually constant diarrhea mixed with blood, of gradual onset. Ulcerative colitis has similarities to Crohn's disease. Ulcerative colitis is an intermittent disease, with periods of exacerbated symptoms, and periods that are relatively symptom-free. Although the symptoms of ulcerative colitis can sometimes diminish on their own, the disease usually requires treatment to go into remission. Ulcerative colitis is treated as an autoimmune disease. Treatment is with anti-inflammatory drugs, immunosuppression, and biological therapy targeting specific components of the immune response. Colectomy (partial or total removal of the large bowel through surgery) is occasionally necessary if the disease is severe, doesn't respond to treatment or if significant complications develop. A total proctocolectomy (removal of the entirety of the large bowel) can be curative, but it may be associated with complications.

Parkinson's disease: Parkinson's disease (also known as Parkinson disease, Parkinson's, idiopathic parkinsonism, primary parkinsonism, PD, hypokinetic rigid syndrome/HRS, or paralysis agitans) is a degenerative disorder of the central nervous system. The motor symptoms of Parkinson's disease result from the death of dopamine-generating cells in the substantia nigra, a region of the midbrain; the cause of this cell death is unknown. Early in the course of the disease, the most obvious symptoms are movement-related; these include shaking, rigidity, slowness of movement and difficulty with walking and gait. Later, cognitive and behavioural problems may arise, with dementia commonly occurring in the advanced stages of the disease. Other symptoms include sensory, sleep and emotional problems.

So far, there is no literature and research showing that the above-mentioned diseases are related to HSV infection. In the present invention, the relationship between the above-mentioned diseases and HSV are provided by the inventor according to the clinical cases for years.

The following context shows common clinical cases of HSV infection, the HSV inspection program, the treating process of HSV infection, the treating drugs of HSV infection and new indications for clinical HSV infection cases.

Common Clinical Case of HSV Infection

The clinical course of HSV infection depends on the age and immune status of the host, the anatomic site involved, and the antigenic virus type. The clinical cases frequently seen are:
 Acute herpetic gingivostomatitis
 Acute herpetic pharyngotonsillitis
 Herpes labialis
 Herpetic whitlow
 Genital herpes: primary, recurrent, or subclinical
 HSV inspection program Several methods that can facilitate the diagnosis of HSV infection are proposed in the present invention.

Tissue culture that shows the characteristic cytopathic effect—ballooning cells and cell death (apoptosis)—is one preferable method to confirm HSV infection. However, the quality of tissue culture is operator—dependent, and it takes 48 hours to run the protocol. Immunofluorescent staining of tissue culture cells can quickly identify HSV and it can distinguish type 1 from type 2.

A Tzanck preparation with a positive finding of balloon cells and multinucleated giant cells containing intranuclear eosinophilic inclusion bodies is a time-honored procedure for assisting in the diagnosis of cutaneous herpesvirus infections.

Hematoxylin-eosin and other special stains after punch biopsy provide more histological information when lesions are possibly superinfected with bacteria or fungi.

Detection of HSV DNA in clinical specimens is possible with polymerase chain reaction (PCR) techniques. PCR is a rapid, noninvasive diagnostic technique for HSV encephalitis and meningitis. It is also useful in detecting asymptomatic viral shedding.

Direct fluorescent antigen (DFA): This procedure requires 2-3 hours. It is used to distinguish HSV-1 from HSV-2 infection.

Antibody testing can demonstrate primary seroconversion, particularly for HSV-1 infection in childhood.

Imaging studies: Brain imaging studies in HSV encephalitis generally demonstrate focal localization in the temporal area; this is associated with edema and contrast enhancement.

Treating Process of HSV Infection

FIG. 1 is a flow chart of a detecting method in the present invention.

Step 100: Checking the disease is a dermatosis or a non-dermotosis. For example, some questions are given for the patient and the skin of the patient is checked by an experienced inspector or a medical staff to determine if the disease is a dermatosis or a non-dermatosis. If the disease is a dermatosis, the inspector or the medical staff will take some samples from an affected part of a patient's skin and the test in step 102 will continue. If the disease is a non-dermatosis, the inspector or the medical staff takes a blood sample of the patient to perform the test in step 104.

Step 102: Performing a Quick Tzanck Test (QTT) process. The QTT process can reveal some histopathological changes from the QTT sample by using a microscope. The inspector or the medical staff can observe some cell's image to confirm the diagnosis with the clinical picture to diagnose viral infection. When the QTT testing's result is "HSV infection", step 106 continues. When the result is "Non-HSV infection", step 108 continues.

Step 104: Performing an immunoglobulin (Ig) testing process, which comprises a HSV IgG process, a Cytomegalovirus immunoglobulin G (CMV IgG) process or a non-specific immunoglobulin E (IgE) process. The CMV IgG/HSV IgG normal titer is smaller than 2 and the non-specific IgE normal titer is smaller than 170 IU/ml. When the testing titer is greater than the normal titer, the process in step 106 is then carried out. Otherwise, the process in step 108 is carried out.

Step 106: Treating an anti-HSV agent, for example, prescribing an anti-HSV medicine or an anti-HSV cream for the patient.

HSV IgG testing is used to detect the presence of the herpes simplex virus in those who have genital sores, encephalitis, and in newborns suspected of having neonatal herpes, a rare but serious condition in which herpes is contracted during birth. A pregnant woman who has been diagnosed with herpes may be monitored regularly prior to delivery to identify a reactivation of her infection, which would indicate the necessity for a caesarean section to avoid infecting the baby. The primary methods of testing for the virus are the herpes culture and HSV DNA testing. Although it is not as sensitive, HSV antibody testing can be used to help diagnose an acute HSV infection if acute and convalescent blood samples are collected. The convalescent blood sample is collected several weeks after the acute sample, and HSV IgG antibody levels are compared to see if they have risen significantly, indicating a current infection.

Cytomegalovirus (CMV) testing is used to determine whether someone with signs and symptoms has an active infection. IgG antibodies are produced by the body several weeks after the initial CMV infection and provide protection from primary infections. Levels of IgG rise during the active infection then stabilize as the CMV infection resolves and the virus becomes inactive. After a person has been exposed to CMV, he or she will have some measurable amount of CMV IgG antibody in their blood for the rest of their life. CMV IgG antibody testing can be used, along with IgM testing, to help confirm the presence of a recent or previous CMV infection. CMV antibody testing may be used to determine immunity to primary CMV infections in people prior to organ or bone marrow transplantation. Since CMV infection is widespread and causes few problems to those with healthy immune systems, general population screening is rarely done.

In this invention, the inventor purposes to take the samples from the lesion through a Quick Tzanck Test (QTT) process, which is no need for washing, thus preserving nearly all the cells of the epidermis and vesicular cavity of the lesion. The QTT stain has staining characteristics similar to those of hematoxylin-eosin, and allows precise interpretation of the cytological changes in the dermal neural network and follicular epithelium. Such cytological changes are usually present and observable at an early stage in herpetic lesions.

Figure 2:
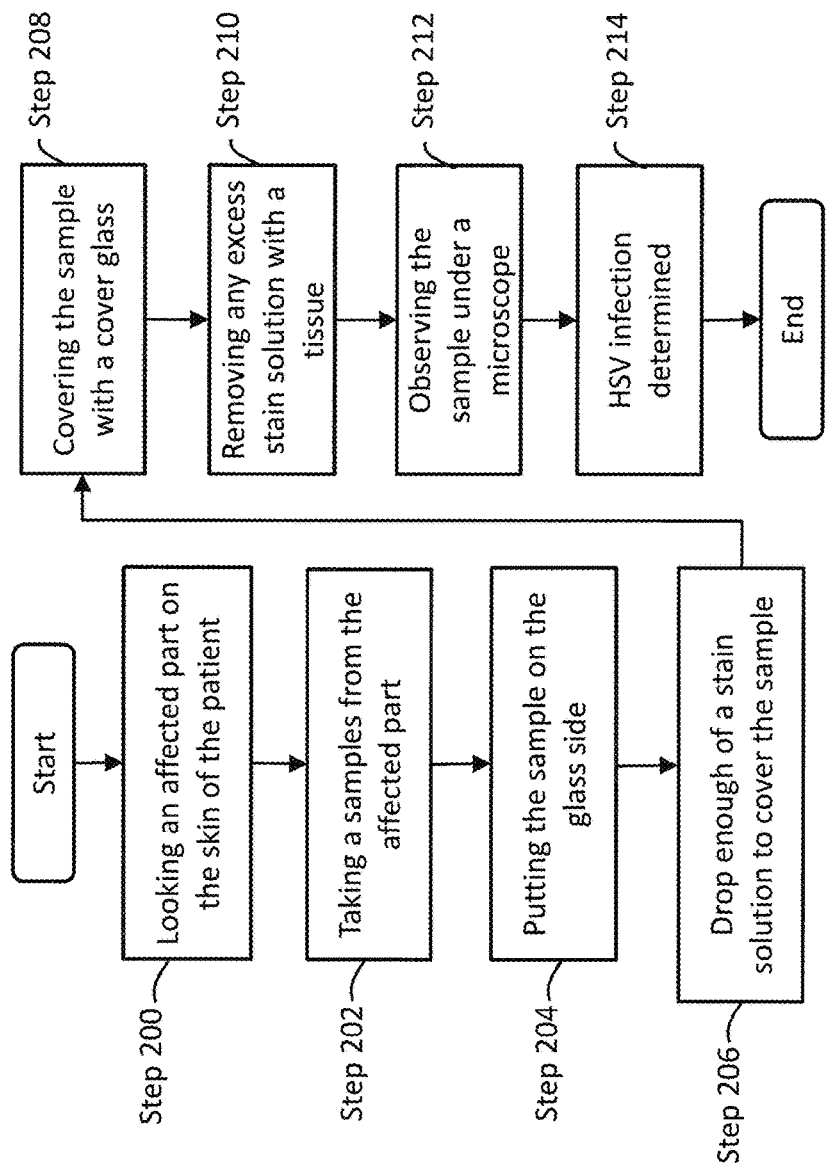
FIG. 2 is a QTT testing flow chart describing a process of smear preparation for the QTT process in the present invention.

FIG. 2 is a QTT testing flow chart describing a process of smear preparation for the QTT process.

Step 200: Finding an affected part, on the skin of the patient, for example, vesicles, pustules, vesicopapules, erosions or scales.

Step 202: Taking a sample from the affected part. The sample is preferably thicker than 50 μm and contains the epidermal sheet and vesicular content with a fine pincer (tip width: 1 mm, without hooks; length: 130 mm).

Step 204: Putting the sample on the glass slide, for example, spreading the sample on a glass slide by gently tapping the sample on the slide with the pincer repeatedly.

Step 206: Dropping stain solution to cover the sample. In one embodiment, the stain solution can be a modified Giemsa stain solution which comprises Giemsa solution, isopropanol and propylene glycol in a ratio of 2:1:1.

Step 208: Covering the sample with a cover glass.

Step 210: Removing excess stain solution from the slide.

Step 212: Observing the sample under a light microscope at least 2 minutes later or within 15 minutes.

Step 214: Determining HSV infection.

In step 214, by observing the QTT sample under a microscope, some histopathological changes can be observed and the viral infection can be diagnosed. The histopathological change, for example, comprises an altered shape, a membrane fusion, inclusion bodies, lysis, and apoptosis, and usually, the change of cell size. The cell size varies from 5-50 micrometers.

Figure 3:
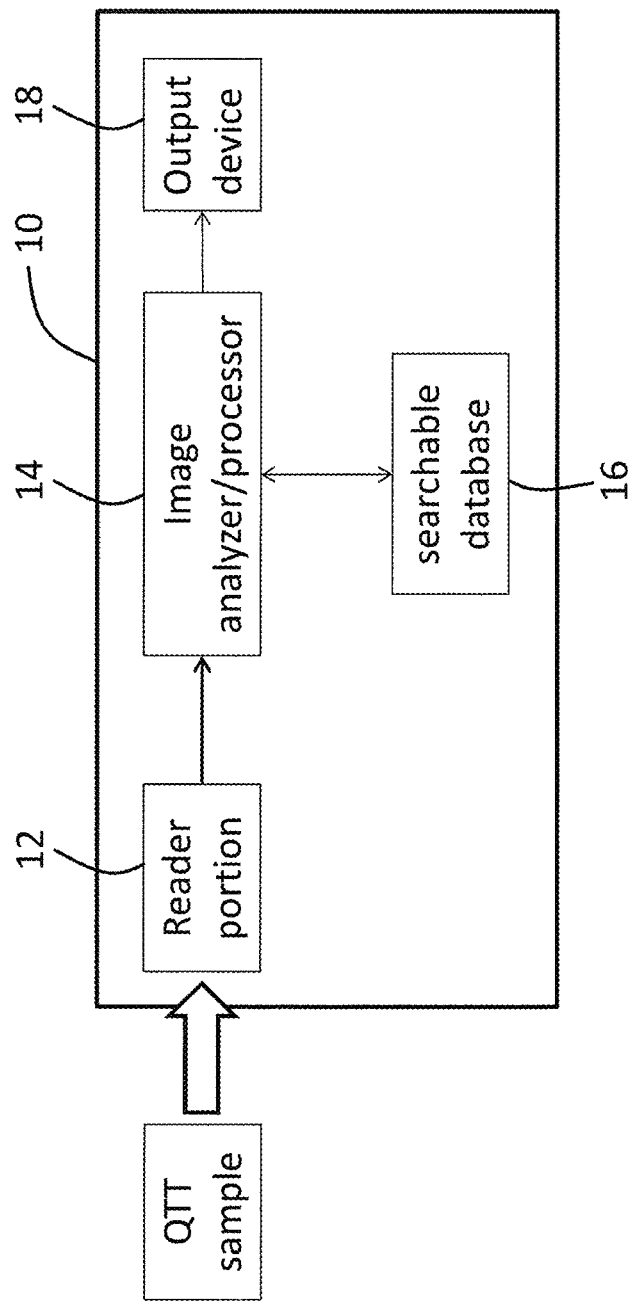
FIG. 3 is a block diagram of a HSV identification imaging system in the present invention.

An identification system may identify some histopathological changes from the QTT sample in a microscope and confirm the diagnosis with the clinical picture to diagnose viral infection. FIG. 3 is a block diagram of a HSV identification imaging system 10 where the methods and procedures of the present invention could be applied. HSV identification imaging system 10 includes a reader portion 12, a image analyzer/processor 14 and a searchable database 16, and an output 18. The reader portion 12 could be any of a number of known systems capable of capturing multiple cell images from a QTT sample and transferring the image data to the image analyzer/processor 14. The HSV identification imaging system 10 can be an identification device that includes an identification software, or an identification machine.

The reader portion 12 may include a microscope device that includes an image sensor, such as a CMOS image sensor, which can capture the images of the cells. The images are transferred to the image analyzer/processor 14.

The image analyzer/processor 14 can create an image model based on the features and characteristics of each image received from the reader portion 12. The image model refers to the areas or images that are indicative of HSV-infected cells. These image models are more than facsimiles of their associated HSV cell's images and include a unique range of data elements that provide analytical opportunities.

At least one image model is compared with the HSV cell's image models in the searchable database 16 by the image analyzer/processor 14 to determine the possibility of HSV infection. The searchable database 16 has a lot of HSV infected cell image models and a lot of images of HSV infection feature. The images of HSV infection feature are used in the cell's model creation process and the HSV cell's image models are used to compare sample cell's model. It is able, by using the HSV cell's images, to quickly and efficiently make a determination, whether the image model corresponding to the contemporaneously captured a cell's image is substantially similar to any of the image models in the searchable database 16. The output device 18 showed the comparison result and analysis data on a display.

Figure 4:
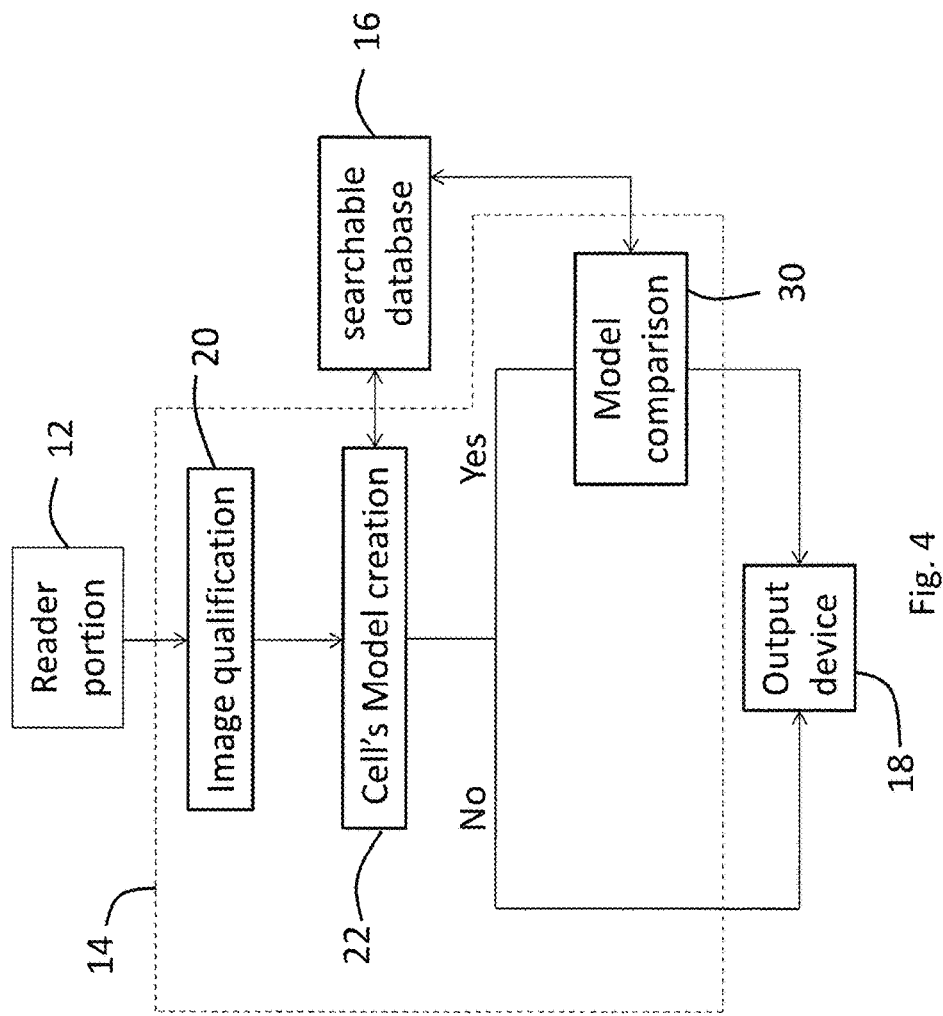
FIG. 4 is a flow diagram illustrating operations to be carried out within the HSV identification imaging system according to the present invention.

FIG. 4 is a flow diagram illustrating operations in the HSV identification imaging system 10, especially in the image analyzer/processor 14, in accordance with an embodiment of the present invention. The process begins when the image analyzer/processor 14 receives image data from reader portion 12. After receiving image data, a series of image qualification functions are performed by the image analyzer/processor 14, as indicated in block 20 in FIG. 4.

Figure 5:
FIG. 5 shows a change from a non-clean cell's image to a clean cell image by a corrected action.
Figure 5:
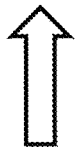
Figure 5:
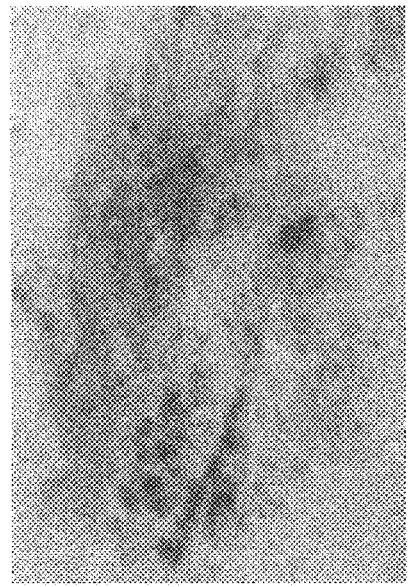

Image qualification 20 involves quickly processing a fraction of the available image data to ensure that the received image is a scan of a real cell's image and of sufficient quality to proceed with processing. In one embodiment, if the image qualification process leads to the conclusion that the cell's image is bad quality, then processing of the image is interrupted. In such a case, the system user is provided with feedback pertaining to identified inadequacies and is allowed to continue processing only when the inadequacies have been corrected. The corrected action comprises an automatic action, such as changing a focus of the microscope or changing an aperture of the microscope. Please refer to FIG. 5. A non-clear cell image (left side) becomes to a clear cell image (right side) by the corrected action. Furthermore, one or two portion of the cell's image are processed during the image qualification 20 in order to expedite processing and to enable feedback to be provided to a system user on a substantially real time basis, wherein the portion of the cell's image comprises an area between 5×5 μm$^2$ and 200×200 μm$^2$ or between 50×50 μm$^2$ and 1000×1000 μm$^2$.

After a clear cell's image has been qualified, as indicated in block 22 in FIG. 4, a cell image model is created. The model creation 22 referred to creating a cell image model by comparing and searching the images of HSV infection feature in the searchable database 16 to see what area in the clear cell image coincide the images of HSV infection feature, and then defining a cell model. Each of the images of HSV infection feature may comprise an image between 5×5 μm$^2$ and 20×20 μm$^2$ or between 50×50 μm$^2$ and 200×200 μm$^2$. In one embodiment, the cell's model of sample comprises at least 5 images of HSV infection feature, or at least 10 images of HSV infection feature or at least 30 images of HSV infection feature.

Figure 6:
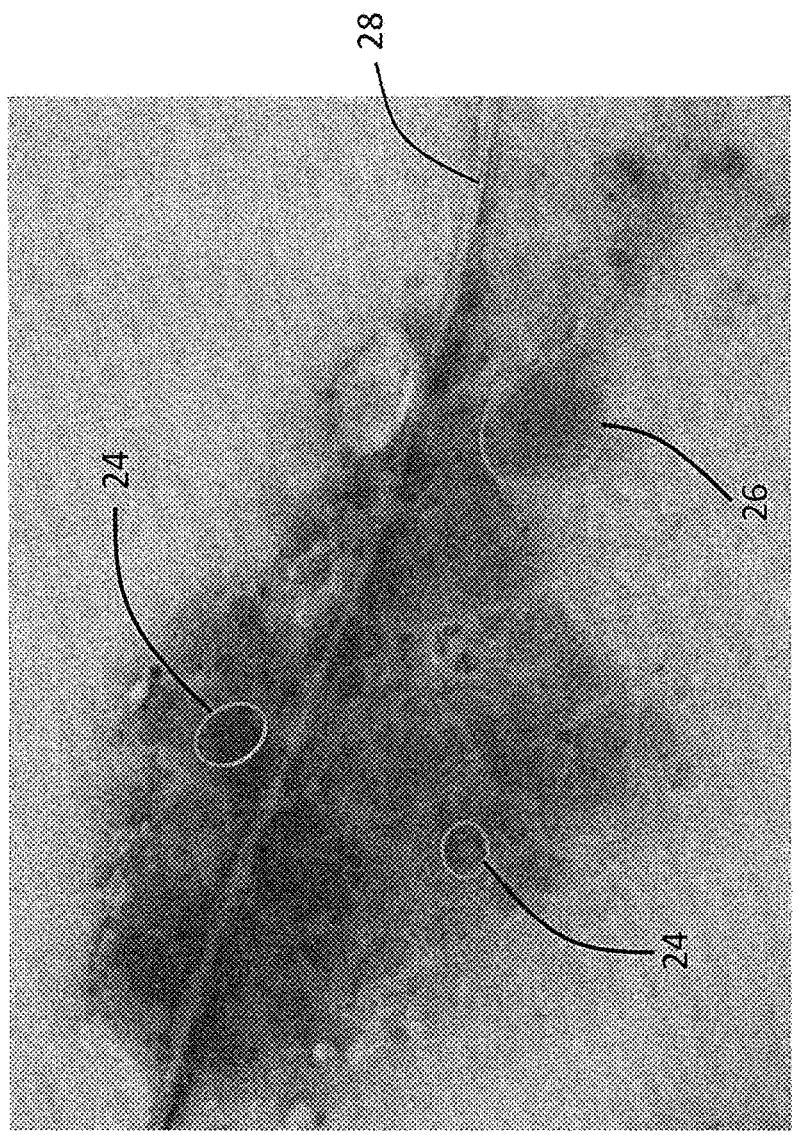
FIG. 6 is a photomicrograph of HSV infected cells showing the balloon cells (BCs) and giant cells (GCs).

Please refer to FIG. 6, which shows one embodiment of the step of cell's model creation. As shown in FIG. 6, the balloon cells (BCs) 24 and the giant cells (GCs) 26 are in an infected nerve end organ 28. The swollen nuclei of the balloon cells (BCs) 24 are slate gray and ground glass in appearance due to margination of the nuclear chromatin. BCs 24 fuse to form giant cells GCs 26. Many nuclei are present in the GCs 26 (original magnification ×400). Portion regions of the BC 24 or portion regions of the GC 26 are the images of HSV infection. In the present embodiment, the BCs 24 and GCs 26 are image model that are indicative of HSV infection.

If no cell's model of sample showing HSV infection is created in the step model creation 22, a "non-HSV infection" message will transfer to the output device 18 from the image analyzer/processor 14.

If one or more cell's model of sample is produced in the step of model creation 22, the cell's model of sample will compare with the HSV cell's image models to confirm HSV infection or not. Model comparison 30 will be described in greater detail below. Model comparison 30 is a process that can be utilized to compare one image model to another. Model comparison 30 is accomplished by applying a series of shift and rotates algorithms to at least one of the image models until a position at which the two models best compare is identified. Then, a score that represents a percentage of data elements that are common between the two image models is computed. Model comparison 30 will transfer an infection score to the output device 18, and then the output device 18 will show the infection score on a display.

The searchable database 16 involves a quick and efficient determination as to which, if any, of a potential thousands, or even millions, of image models within searchable database 16 exhibits a desired level of similarity, as compared to a target image model. In accordance with one embodiment, the target image model is an image model associated with a contemporaneously image. Rather than comparing image models specifically, a set of database keys that describe different image model characteristics are defined and enable general, rather than specific comparisons to be made during the searchable database 16 process. The desired level of similarity is adjustable and could be selected based on a desired processing speed, a desired level of security, and other characteristics indicative of the environment for which system 10 is designed to provide security.

The Treating Drugs of HSV Infection

Early treatment with antiviral agents can reduce morbidity and prevent complications. According to one feature of the present anti-HSV agent provide the compound of formula (I)

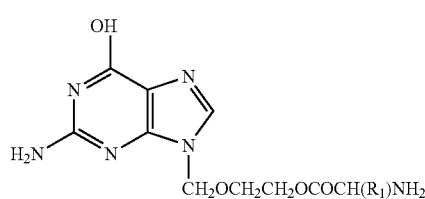

(I)

wherein $R_1$ represents a group of formula —CH[CH$_3$]$_2$ and pharmaceutically acceptable salts thereof. The compound of formula (I) can also be named as 2-[(2-amino-6-oxo-6,9-dihydro-3H-purin-9-yl)methoxy]ethyl-2-amino-3-methylbutanoate. As used herein, the compounds according to the anti-HSV agent will be intended to include the compound of formula (I) and its pharmaceutically acceptable salts.

The pharmaceutically acceptable salts of the compound of formula (I) are preferably acid addition salts derived from an appropriate acid, e.g. hydrochloric, sulphuric, phosphoric, maleic, fumaric, citric, tartaric, lactic, acetic or p-toluenesulphonic acid. Particularly preferred salts are the hydrochloride salts of compound of formula (I).

The compounds according to the anti-HSV agent may be prepared in conventional manner, e.g., by a process as described below.

Thus, according to a further feature of the present anti-HSV agent provide a process for the preparation of the compound of formula (I) above and pharmaceutically acceptable salts thereof which comprises (a) reacting a compound of formula (II)

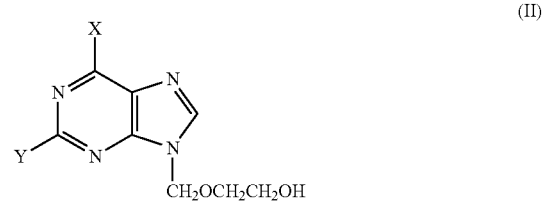

(II)

wherein X is an optionally protected hydroxy group, and Y is an optionally protected amino group with an optionally protected valine or a functional equivalent thereof;

(b) converting a compound of formula (III)

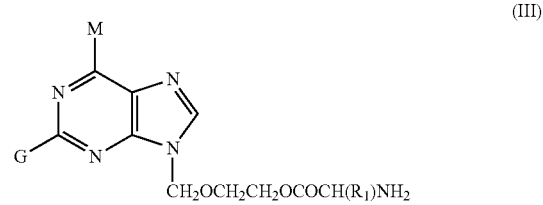

(III)

(wherein $R_1$ is as defined above; and M represents a hydroxy group and G represents an atom or group that can be replaced by or converted to an amino group; or G represents an amino group and M represents an atom or group that can be replaced by or converted to a hydroxy group) into a compound of formula (I) or a pharmaceutically acceptable salt thereof; or (c) reacting a compound of formula (IV)

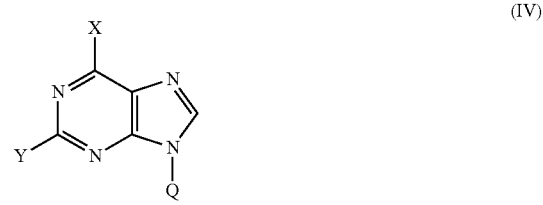

(IV)

(wherein X and Y are as defined above and Q represents a leaving atom or group) with a compound of formula (V)

ACH₂OCH₂CH₂OCOCH(R₁)R₂ (V)

(wherein R₁ is as defined above, A represents a leaving group or atom and R₂ is an optionally protected amino group); and optionally effecting one or more of the following conversions;
(i) removal of any protecting groups;
(ii) where the resulting product is a compound of formula (I), conversion of the said compound into a pharmaceutically acceptable salt thereof; and
(iii) where the resulting product is a pharmaceutically acceptable salt of a compound of formula (I), conversion of the said salt into the parent compound.

With regard to process (a), the esterification reaction may be carried out in conventional manner, for example in a solvent such as pyridine or dimethylformamide in the presence of a coupling agent such as N,N'-dicyclohexylcarbodiimide, optionally in the presence of a catalytic base such as 4-dimethylaminopyridine. The water formed during the reaction may, if desired, be removed in conventional manner, for example by distillation or by the addition of a water-binding substance. Subsequently, the ester obtained as reaction product may be isolated in conventional manner.

As an alternative to the use of valine per se, a functional equivalent of the acid may be employed, e.g., an acid halide such as the acid chloride, or an acid anhydride. In such a case in order to avoid undesirable side-reactions, it is advantageous to use an amino-protected derivative. Examples of preferred amino-protecting groups including acyl, e.g., C₁₋₄ alkanoyl such as acetyl and aryloxycarbonyl, e.g., benzyloxy carbonyl. A suitable amino-protected derivative, for example, is one wherein the amino group of the amino acid is replaced by an azido group.

Conversion of a compound of formula (III) into a compound of formula (I), by method (b), can be achieved by various means. For example G may represent an azide group which can be reduced to an amino group by catalytic hydrogenation, using a suitable catalyst such as palladium on carbon. Alternatively, G may each represent a halogen atom or an alkylthio or alkylsulphonyl group which can be converted to an azide group which in turn can be converted to an amino group by catalytic hydrogenation using, for example, hydrogen in the presence of palladium on carbon. For the preparation of the compound of formula (I), a compound of formula (III) wherein M is an amino group may be converted to a hydroxy group for example by treatment with a deaminating enzyme such as adenosine deaminase.

In process (c), the group Q in formula (IV) may, for example, represent a hydrogen atom; an acyl group, e.g. a C₁₋₄ alkanoyl group such as an acetyl group or an aroyl group such an a benzoyl group; or a tri-C₁₋₄ alkylsilyl group such as a trimethylsilyl group. The group A in formula (V) may, for example, represent a halogen atom (e.g. chlorine) or an acyloxy group wherein the acyl moiety may be, for example, a C₁₋₄ alkanoyl group such as acetyl or an aroyl group such as benzoyl. The group R₂ may represent an amino-protecting group such as for example, C₁₋₄ alkanoyl (e.g., acetyl) or aryloxycarbanoyl (e.g., benzyloxycarbonyl) it may also represent an azido group. The reaction may be conveniently effected in a strong polar solvent such as dimethylformamide or hexamethylphosphoramide, advantageously in the presence of a base such as triethylamine or potassium carbonate. Alternatively, a thermal condensation may be effected by heating the compounds of formulae (IV) and (V) in the presence of a catalytic amount of a strong acid, e.g., sulphuric acid.

Compounds of formulae (II) to (V), employed as intermediates in the synthesis of the compound of formula (I), can be prepared in conventional manner, e.g., by procedures described in U.K. Patent Specification No. 1523865. These methods rely on intermediates prepared from simply substituted purines, which may be available commercially, or prepared according to techniques which are well known per se and which are disclosed in the literature such as the aforementioned text-book. Thus, for example, compounds of formula (III) may be generally prepared by using an analogous procedure to that of process (c), i.e., reacting an appropriate purine with a compound of formula (V).

The optional conversions (i), (ii) and (iii) may be effected in conventional manner. Thus, for example, removal of protecting groups in conversion (i) may be effected by hydrolysis, solvolysis or hydrogenolysis as appropriate. With regard to removal of protecting groups on the amino acid acyl radicals, hydrogenolysis, e.g., of aryloxycarbonyl protecting groups, and conversion of azido group, e.g., by catalytic hydrogenation, e.g., using a palladium catalyst, are preferred. With regard to protection of the groups in the 2- and/or 6-positions of purine nucleus, these may be selected for example from arylmethyl groups, e.g., benzyl; or tri-C₁₋₄ alkylsilyl, e.g., trimethylsilyl. Arylmethyl blocking groups, may be removed for example by hydrogenolysis, e.g., by hydrogenation in the presence of Raney nickel or a palladium catalyst. Trialkylsilyl blocking groups may be removed for example by solvolysis, e.g., by alcoholysis.

The conversion of a compound of formula (I) into a pharmaceutically acceptable salt may be effected in conventional manner, for example, by treatment of the compound with an appropriate acid to form an acid addition salt, for example, by lyophilisation of a methanolic solution of the parent ester with an acid solution.

Similarly, conversion of a salt into the parent compound of formula (I) may be effected in conventional manner.

The present anti-HSV agent, or the combination thereof also provides the compounds of formula (I) and pharmaceutically acceptable salts thereof (hereinafter identified as "the active compounds") for use in medical therapy, e.g., in the treatment of a viral disease in an animal, e.g., a mammal such as a human. The compounds are especially useful for the treatment of diseases caused by various DNA viruses, such as herpes infections, for example, herpes simplex, varicella or zoster, cytomegalovirus as well as diseases caused by hepatitis B or Epstein-Barr viruses or human herpes virus-6 (HHV-6). The active compounds, i.e. the anti-HSV agent, can also be used for the treatment of papilloma or wart virus infections, for example, for the treatment of cervical cancer and oral cancer. Besides, the active compounds, i.e. the anti-HSV agent, can be used for the treatment of retrovirus infections such as HIV infections in synergistic combination with anti-HIV agents.

In addition to their use in human medical therapy, the compounds of formula (I) can be administered to other animals for treatment of viral diseases, e.g., in other mammals. For example, the active compounds are especially useful for the treatment of equine rhinopneumonitis.

The present anti-HSV agent also provides a method for the treatment of a viral disease in an animal, e.g., a mammal such as a human, which comprises administering to the animal an effective antiviral amount of a compound of formula (I) or a pharmaceutically acceptable salt thereof.

The present anti-HSV agent also provides the use of a compound of formula (I) in the manufacture of a medicament for the treatment of a viral infection.

The active compounds may be administered by any route appropriate to the condition to be treated, suitable routes including oral, rectal, nasal, topical (including buccal and sublingual) vaginal and parenteral (including subcutaneous, intramuscular, intravenous, intradermal, intrathecal and epidural). It will be appreciated that the preferred route may vary with for example the condition of the recipient.

For each of the above-indicated utilities and indications the amount required of an active ingredient (as above defined) will depend upon a number of factors including the severity of the condition to be treated and the identity of the recipient and will ultimately be at the discretion of the attendant physician or veterinarian. In general however, for each of these utilities and indications, a suitable effective dose will be in the range 0.1 to 250 mg per kilogram bodyweight of recipient per day, preferably in the range 1 to 100 mg per kilogram bodyweight per day and most preferably in the range 5 to 20 mg per kilogram bodyweight per day; an optimum dose is about 10 mg per kilogram bodyweight per day. (Unless otherwise indicated, all weights of active ingredient are calculated as the parent compound of formula (I): for salts thereof the figures would be increased proportionately.) The desired dose is preferably presented as two, three, four or more sub-doses administered at appropriate intervals throughout the day. These sub-doses may be administered in unit dosage forms, for example, containing 10 to 1000 mg, preferably 20 to 500 mg and most preferably 100 to 400 mg of active ingredient per unit dosage form.

The compounds of the present anti-HSV agent may be administered alone or in combination with other therapeutic agents, for example, with 2-Amino-1,9-dihydro-9-((2-hydroxyethoxy)methyl)-6H-purin-6-one (acyclovir) or 2-[(2-amino-6-oxo-6,9-dihydro-3H-purin-9-yl)methoxy]ethyl-2-amino-3-methylbutanoate (valacyclovir) used to treat herpes virus infections in particular HSV.

The acyclovir formula (VI) is showed below:

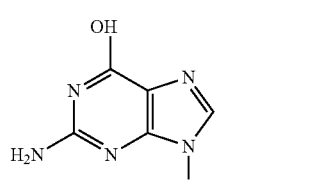

(VI)

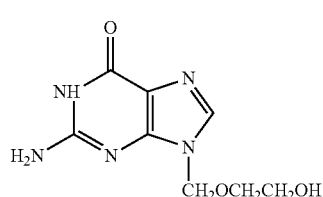

(VI)

The valacyclovir formula (VII) is showed below:

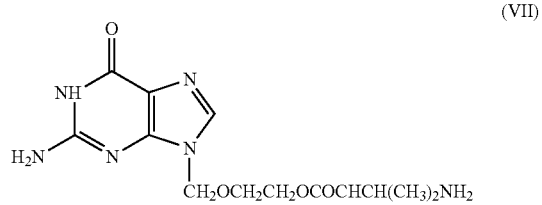

(VII)

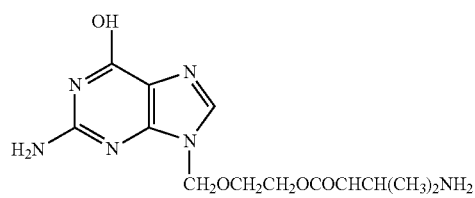

(VII)

Acyclovir is an antiviral drug. It slows the growth and spread of the herpes virus so that the body can fight off the infection. Acyclovir will not cure herpes, but it can lessen the symptoms of the infection.

Acyclovir is used to treat infections caused by herpes viruses. Illnesses caused by herpes viruses include genital herpes, cold sores, shingles, and chicken pox.

Acyclovir differs from previous nucleoside analogues in containing only a partial nucleoside structure: the sugar ring is replaced with an open-chain structure. It is selectively converted into acyclo-guanosine monophosphate (acyclo-GMP) by viral thymidine kinase, which is far more effective (3000 times) in phosphorylation than cellular thymidine kinase. Subsequently, the monophosphate form is further phosphorylated into the active triphosphate form, acyclo-guanosine triphosphate (acyclo-GTP), by cellular kinases. Acyclo-GTP has approximately 100 times greater affinity for viral than cellular polymerase. As a substrate, acyclo-GTP is incorporated into viral DNA, resulting in premature chain termination. Although acyclovir resembles a nucleotide, it has no 3' end. Therefore, after its incorporation into a growing DNA strand, no further nucleotides can be added to this strand. It has also been shown that viral enzymes cannot remove acyclo-GTP from the chain, which results in inhibition of further activity of DNA polymerase. Acyclo-GTP is fairly rapidly metabolised within the cell, possibly by cellular phosphatases. In sum, acyclovir can be considered a prodrug: it is administered in an inactive (or less active) form and is metabolised into a more active species after administration.

Valacyclovir is a prodrug that is nearly completely converted to Acyclovir and L-valine. Due to its more efficient phosphorylation by viral thymidine kinase, Acyclovir's antiviral activity is greatest against herpes simplex virus type 1 (HSV-1), followed by herpes simplex virus type 2 (HSV-2), varicella-zoster virus (VZV), Epstein-Barr virus (EBV), and cytomegalovirus (CMV).

Valacyclovir is rapidly and nearly completely (99%) converted to the active compound, acyclovir, and L-valine by first-pass intestinal and hepatic metabolism by enzymatic hydrolysis. Acyclovir is converted to inactive metabolites by alcohol and aldehyde dehydrogenase and, to a small extent, by aldehyde oxidase. The metabolism of valacyclovir and acyclovir is not associated with hepatic microsomal enzyme systems.

While it is possible for the active ingredients to be administered alone, it is preferable to present them as pharmaceutical formulations. The formulations, both for veterinary and for human use, of the present anti-HSV agent comprise at least one active ingredient, as above defined, together with one or more acceptable carriers therefor and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers of finely divided solid carriers or both, and then, if necessary, shaping the product.

Formulations of the above-mentioned anti-HSV agent suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion; or as a preventive vaccine; or as a spray gas; or as a skin care products; or as a skin cleaning products. For some applications, the above-mentioned anti-HSV agent can be one of the ingredients in a shampoo or hair restorer for improving or curing user's Alopecia or preventing the user from catching Alopecia. The above-mentioned anti-HSV agent can be one of the ingredients in a soap, facial cleanser or cleaning cream for improving or curing user's dermatoses or for preventing the user from catching specific dermatoses. The active ingredient may also be presented as a bolus, electuary or paste.

Furthermore, the anti-HSV agent can include, for example, valacyclovir, penciclovir, famciclovir, Foscarnet, Cidofovir (HPMPC, GS-504), Trifluridine, Lobucavir, Crofelemer or Resiquimod except acyclovir and valacyclovir, but is not limited thereto.

Figure 7:
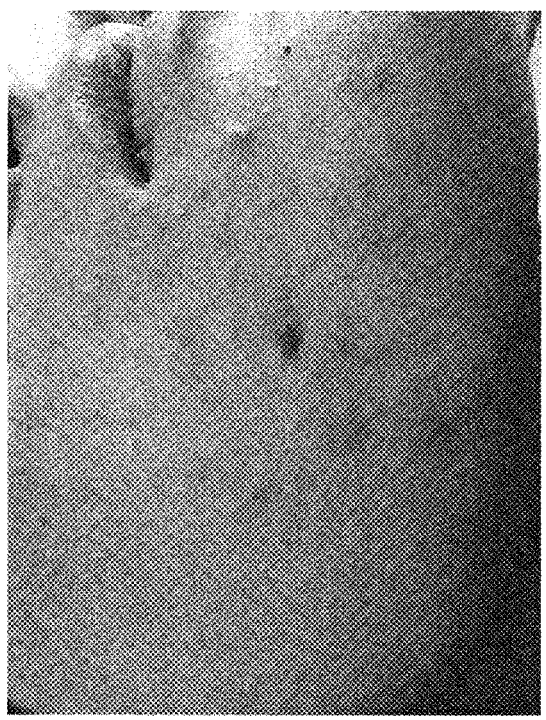
FIG. 7 is a picture showing 1st clinical case of acne before treatment.

Proposed dose of the antiviral agent prescribed for HSV infection:
1. Adult: Valacyclovir (500 mg)
   a. 2 tablets daily (i.e. 1 tablet after breakfast and dinner) for 5-7 days.
   b. 3 tablets daily (i.e. every 8 hours) for severe cases in the beginning only.
2. Children: Acyclovir granules 10 mg/KG, every 6 hours, for 5-7 days
3. Prescribed topical corticosteroids ointment or cream New Indications for Clinical HSV Infection Cases 1$^{st}$ Clinical Case of Acne Before the treatment: FIG. 7 is a patient presented with many painful pustules over her face especially around her mandible for 3 months. The pus was proved to be positive for HSV by polymerase chain reaction (PCR).

Figure 8:
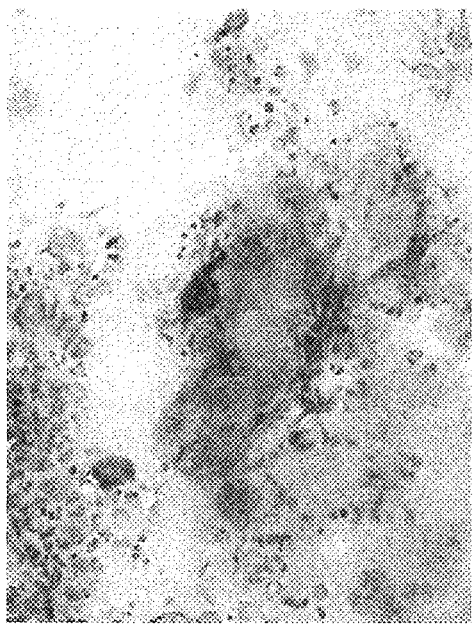
FIG. 8 is a photomicrograph of cells of $1^{st}$ clinical case of acne.
Figure 8:

FIG. 8 is an image of QTT sample which from the same pustule revealing that a dermal nerve fiber (DNF) is surrounded by many balloon cells (BCs). There were other similar degenerated Schwann cells groups. High magnification demonstrated many BCs with large and pleomorphic nuclei. The pathologic findings together with the result of the PCR confirmed that these pustules originated from HSV infection.

Figure 9:
FIG. 9 is a picture showing $1^{st}$ clinical case of acne after treatment.

Diagnosis: acne induced by HSV infection
Prescriptions:
Valacyclovir: 2 tablets daily for 5 days
Nadifloxacin cream for 5 days
After the treatment: FIG. 9 is an affected part of the patient after the treatment. The number of the pustules and the extent of inflammation decreased 5 days later.

2$^{nd}$ Clinical Case of Acne

Figure 10:
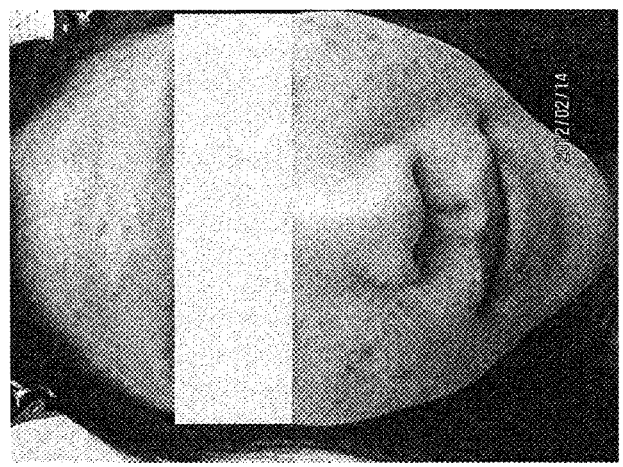
FIG. 10 is a picture showing $2^{nd}$ clinical case of acne before treatment.

Before the treatment: FIG. 10 is a patient presented with many reddish-brown pustules and pigmented spots over her face for one month.

The QTT sample from a pustule revealed long, degenerated DNFs were surrounded by many BCs. The patient was diagnosed as acne-like eruption originated from HSV infection.

Figure 11:
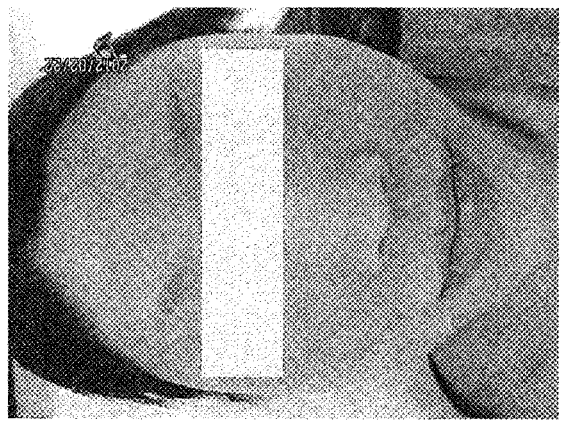
FIG. 11 is a picture showing $2^{nd}$ clinical case of acne after treatment.

Diagnosis: acne induced by HSV infection
Prescriptions:
Valacyclovir: 2 tablets daily for 5 days
Acyclolidofenac (ADO) ointment
After the treatment: FIG. 11 is an affected part of the patient after the treatment. Nearly no pustules were seen 8 days later. Her skin became finer and whiter.

3$^{rd}$ Clinical Case of Acne

Figure 12:
FIG. 12 is a picture showing $3^{rd}$ clinical case of acne before treatment.
Figure 12:

Before the treatment: FIG. 12 is a patient presented with many comedoes, pustules combined with severe inflammation over his nose for 5 months.

The QTT sample from a pustule revealed long, degenerated DNFs were surrounded by many BCs. Giant cells (GCs) and melanin pigments are also found.

Figure 13:
FIG. 13 is a picture showing $3^{rd}$ clinical case of acne after treatment.
Figure 13:
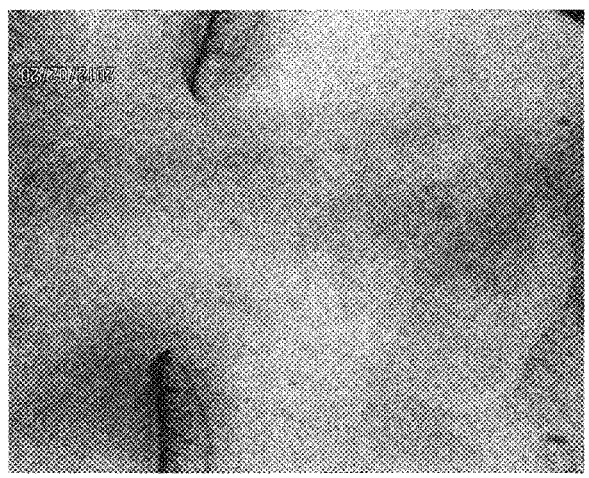

HSV IgG enzyme immunoassay titer (normal <2.0): 53.1
Diagnosis: acne induced by HSV infection
Prescriptions:
Antiviral agent: Valacyclovir 2 tablets daily for 5 days per month.
ADO ointment
After the treatment: FIG. 13 is an affected part of the patient after the treatment. The severe inflammation on the nose and over the left cheek decreased a lot. The number of the white comedoes also decreased 23 days later.

4$^{th}$ Clinical Case of Acne

Figure 14:
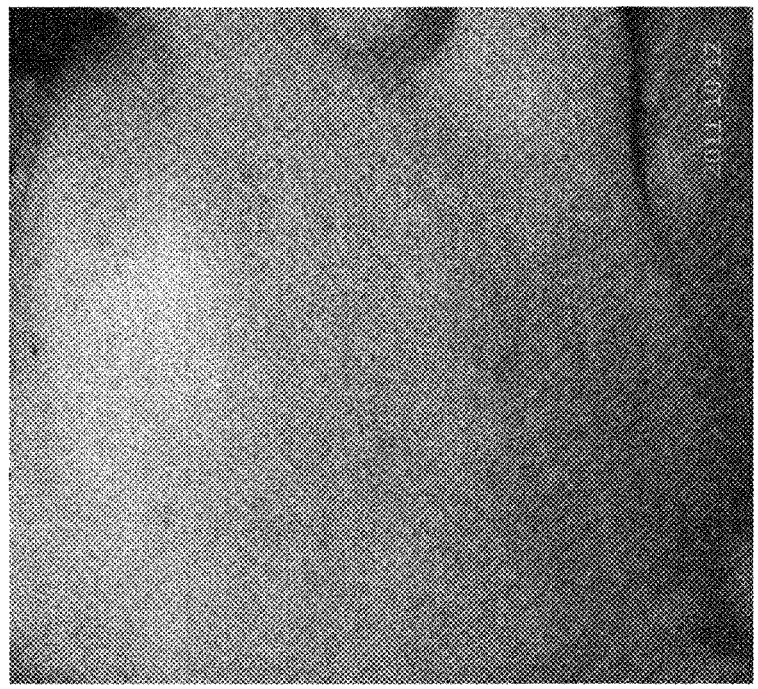
FIG. 14 is a picture showing $4^{th}$ clinical case of acne before treatment.

Before the treatment: FIG. 14 is a patient presented with many itchy pin-head-size pustules appearing suddenly over her face. The eruption appeared suddenly after she applied new kind of skin lotion over her face.

Figure 15B:
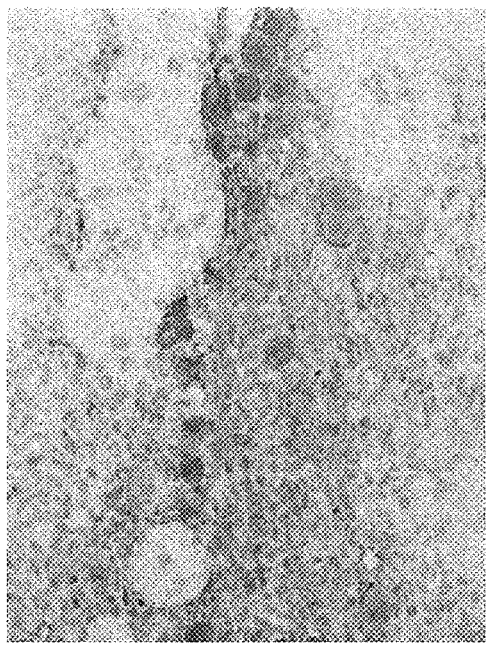
FIG. 15a-FIG. 15b are photomicrographs of cells of $4^{th}$ clinical case of acne.
Figure 15A:
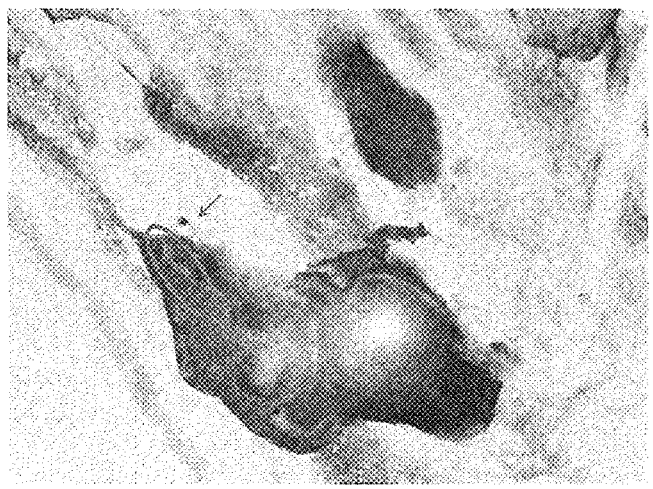

FIG. 15a is an image of QTT sample revealing a degenerated nerve (circle) and hair (arrow) are observed in an enlarged hair follicle due to dense inflammatory infiltration.

FIG. 15b is an image of QTT sample revealed a BC with thick cell membrane and intranuclear eosinophilic inclusion body (EIB). Some BCs gathered together to form balloon cell nests (BCNs).

Figure 16:
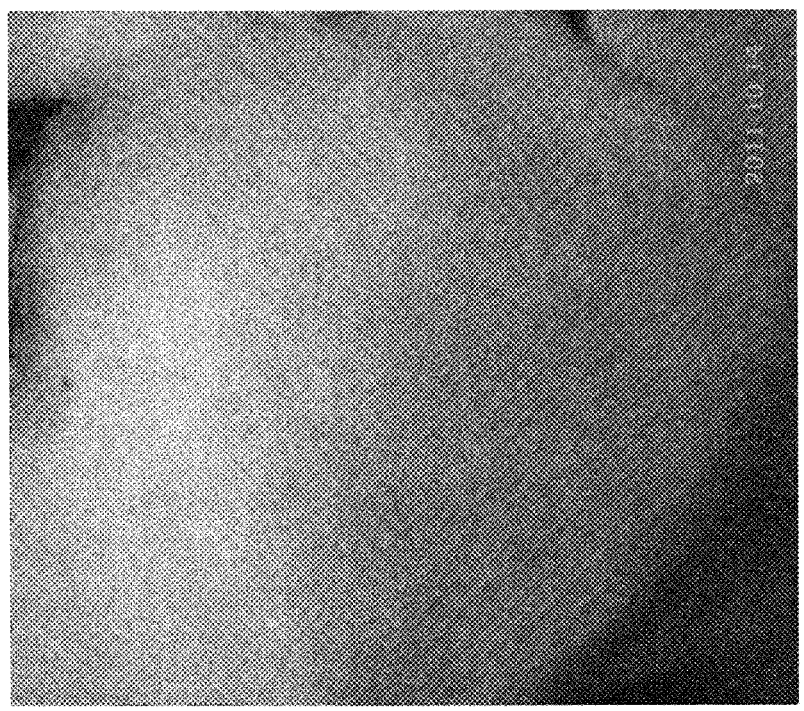
FIG. 16 is a picture showing $4^{th}$ clinical case of acne after treatment.

Diagnosis: acne (multiple pustular type) induced by HSV infection
Prescriptions:
Valacyclovir: 2 tablets daily for 5 days
Anti-allergic agent for 7 days
Gr. IV topical corticosteroids (CS)
After the treatment: FIG. 16 is an affected part of the patient after the treatment. Not only the number but also the size of the pustules decreased a lot 2 days later. After completed the prescribed medication, there is no recurrence till now (about one year).

5$^{th}$ Clinical Case of Acne

Figure 17:
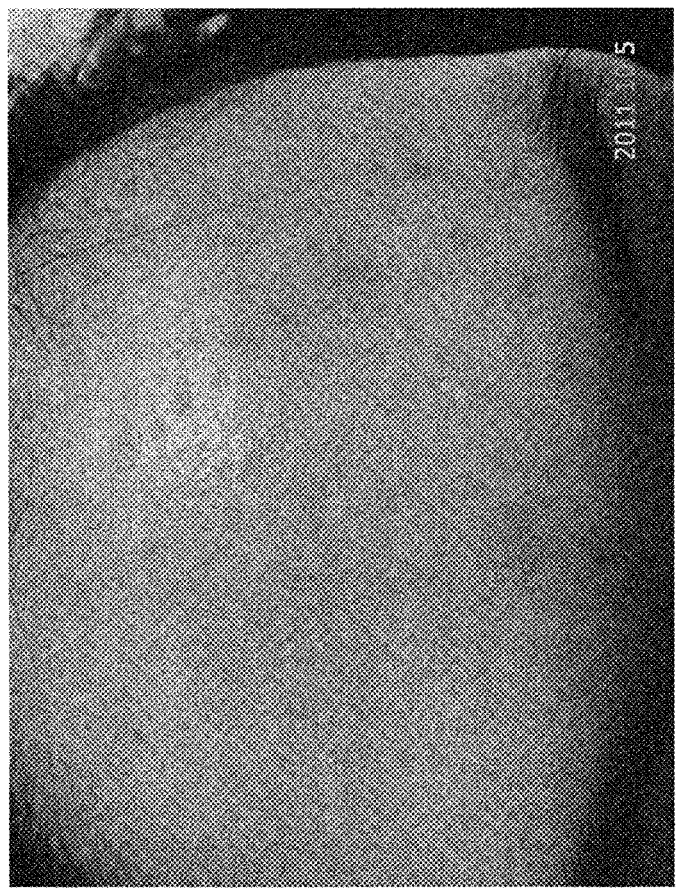
FIG. 17 is a picture showing $5^{th}$ clinical case of acne before treatment.

Before the treatment: FIG. 17 is a patient presented with many small red vesicopapules and pustules over her forehead, both cheeks for 2 weeks.

Figure 18A:
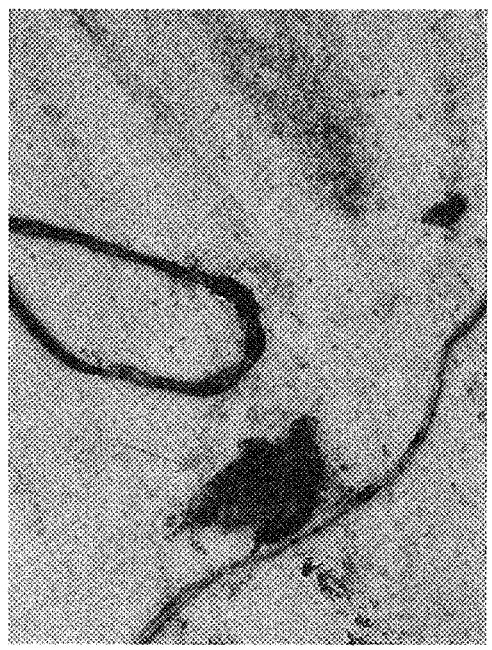
FIG. 18a-FIG. 18b are photomicrographs of cells of $5^{th}$ clinical case of acne.

FIG. 18a is an image of QTT sample revealing that a large BC nest (arrow) was observed surrounded one of the 2 demyelinated DNFs.

Figure 18B:
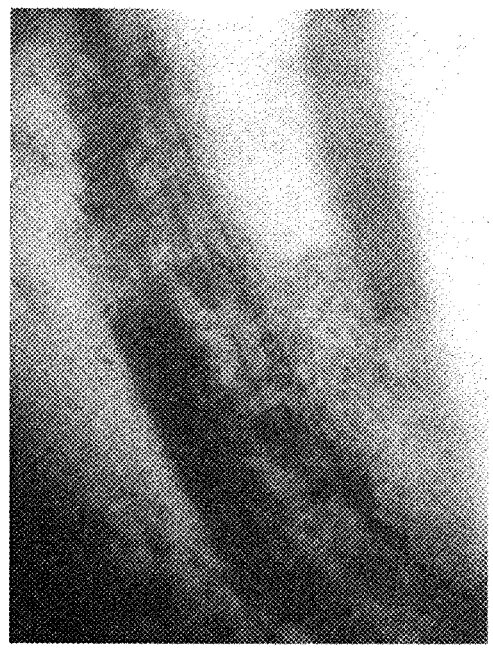

FIG. 18b is an image of QTT sample revealed BCs of various sizes surrounded 2 demyelinated DNFs.

Figure 19:
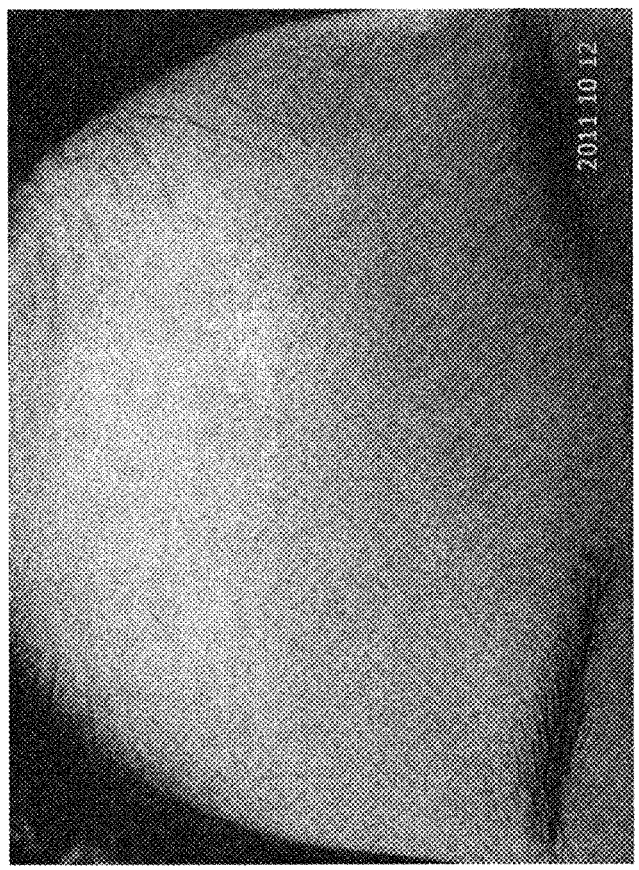
FIG. 19 is a picture showing $5^{th}$ clinical case of acne after treatment.

Diagnosis: acne induced by HSV infection
Prescriptions:
Valacyclovir: 2 tablets daily for 5 days
Antibiotics 2 days
Nadifloxacin cream After the treatment: FIG. 19 is an affected part of the patient after the treatment. Symptoms have significantly improved 7 days later.

6$^{th}$ Clinical Case of Acne

Figure 20:
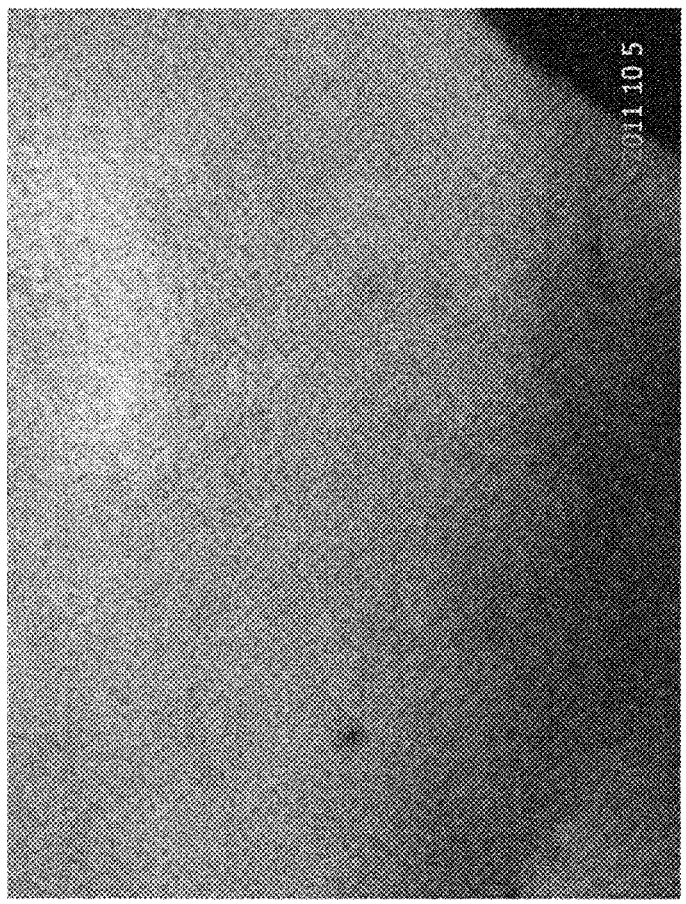
FIG. 20 is a picture showing $6^{th}$ clinical case of acne before treatment.

Before the treatment: FIG. 20 is a patient presented with many red inflamed nodules over her face for 1 week. She also complained of pain over her cheeks and itching over her mandible.

Figure 21B:
FIG. 21a-FIG. 21b are photomicrographs of $6^{th}$ clinical case of acne.
Figure 21A:
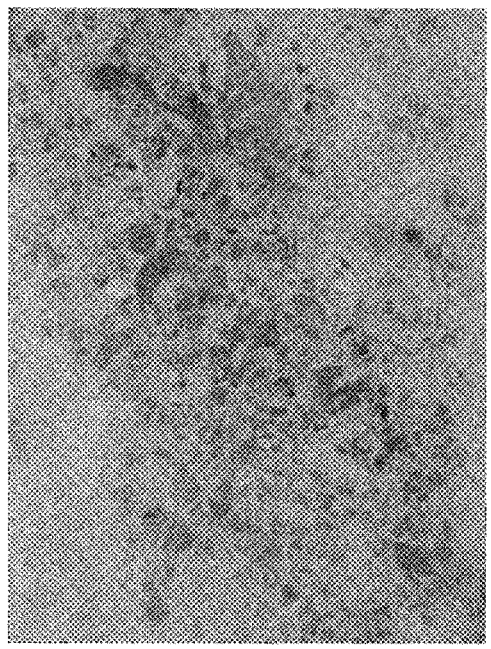

FIG. 21a is an image of QTT sample revealed BCs with EIBs and scattering BCNs.

FIG. 21b is an image of QTT sample revealed many longitudinal, large BCs and inflammatory infiltration by neutrophils (circles).

Figure 22:
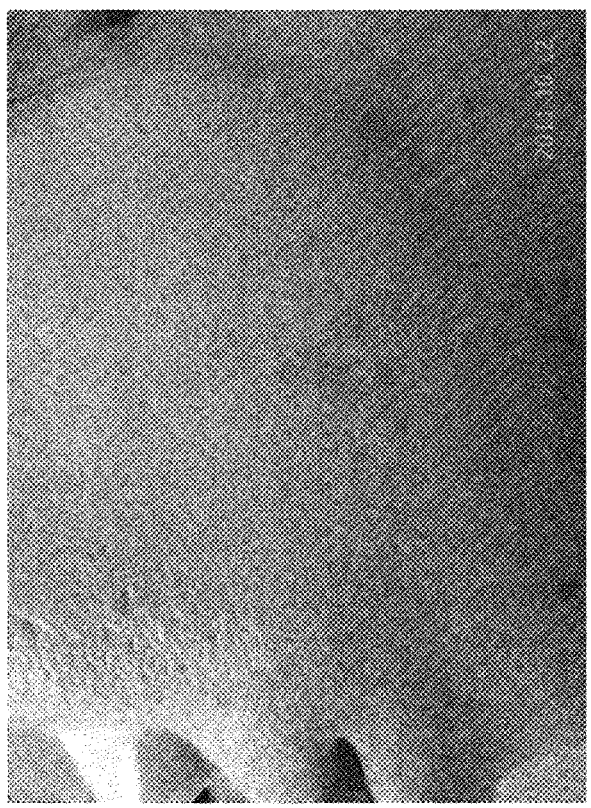
FIG. 22 is a picture showing $6^{th}$ clinical case of acne after treatment.

Diagnosis: acne induced by HSV infection
Prescriptions:
Valacyclovir: 2 tablets daily for 5 days
Nadifloxacin cream
Gr. IV topical CS After the treatment: FIG. 22 is an affected part of the patient after the treatment. Symptoms have significantly improved 7 days later.

Above 6 patients presented with clinical picture of acne that have long been thought to be due to bacterial infection. However, the pathologic findings together with the result of the PCR confirmed that these pustules and red papules are caused by HSV infection.

3 days after intraperitoneal inoculation of HSV in Albino mice, general weakness and/or marked paralysis of the hind limbs developed (Yamamoto et al., Acta neuropath (Berl.) 26, 285-299 (1973)). Yamamoto et al. confirmed that neurons, astrocytes, oligodendrocytes and Schwann cells were infected. The endothelial cell, perineural fibrocyte and smooth muscle cells could also be infected. Affection of the hemispheres and cerebellum was limited, while pontobulbar, spinal lesions were severe and extensive. The site of virus replication in the peripheral nervous system was primarily in neurons, but replication occurred with great frequency in Schwann cells. This study documented that HSV is a systemic infection. The Schwann cells were infected and served as a mediating role in the spread of the HSV along peripheral nerve fibers to the central nervous system. The inflammatory infiltration surrounding the degenerated DNFs and ballooning Schwann cells in the QTT of patients suffering from acne may represent the immune reaction to excrete the HSV-infected cells through skin in order to protect central nervous system. Since the skin is the most external part of the nervous system, acne may represent the excretion of the HSV-infected cells after the maturation of one's immune system during adolescence.

The innervations of the hair follicle are the most complex and thus thoroughly studied among the cutaneous sensory receptors. It is because the innervations of the hair follicles arising from the myelinated stem axons in the deep dermal plexus together with the Pacinian corpuscles are the deepest sensory receptors. Pacinian corpuscles are the largest sensory corpuscles found not only in the palmar and plantar aponeurosis or genitalian deep to the skin and also present in ligaments and joint capusles (Munger et al., Arch Histol Cytol. 51, No 1, 1-34 (1988)).

Arthritis can thus be elicited by the HSV infection of the Pacinian corpuscles in ligments and joint capsules as the acne-like eruption does in the skin. Actually the acne in adolescence could be self-limited but its fulminate type may combine fever and multiple joint pains (Medscape, Acne Fulminate Mar. 29, (2011)). Increase level of substance P has been documented in the synovial fluid and serum of patients with rheumatoid arthritis (Marshall et al., Arthiritis Pherma 33 (1): 87-90 (1990); Menkes et al, J Rheumatol 20 (4): 714-17 (1993)). Substance P stimulates prostaglandin E2, and collagenase release from the rheumatoid synoviocytes. These findings were reported to be responsible for the pannus formation in rheumatoid patients (Lotz et al., Science 235; 893-895 (1987)). After the disclosure of the pathologic changes causing acne in the Schwann cells of the DNFs, it is worthwhile to examine the pathologic changes in the diseased joints by QTT in this invention. There is a great chance to find a primary lesion in the sensory receptors and peripheral nerve fibers in the joints.

Substance P and other neuropeptides can be released from the peripheral sensory nerve fibers in the skin, muscle and joint in response to certain types of infection or injury and induce a local inflammatory (Donkin J J et al., Progress in brain research, 161:97-109 (2007)). In other words, the ballooning Schwann cells, desheathing DNFs induce by HSV infection followed by an inflammatory reaction mediated by neurogenic peptides in order to decrease the HSV-infected cells. However, if the HSV infected cells are too less to induce vesicles or pustules, the severe inflammatory reaction may lead a clinical mis-diagnosis of etiology unknown dermatitis, acne and arthritis. The QTT is the quickest method to diagnose the underlying HSV infection in various organs and is able to bring about an early treatment by the antiviral agents.

The tumor necrosis factor-alpha inhibitors are the most potent treatment for the rheumatoid arthritis around 2000. However, there are many reports concerning the adverse cutaneous reaction secondary to treatment for rheumatiod arthritis with tumor necrosis factors—alpha inhibitors after 2000. Two patients with erythema multiforme (Soliotis F et al., Ann Rheum Dis 61: 850-1, 2002; Vergara G et al, Arch Dermatol 138: 1258-9, 2002), one with atopic dermatitis-like eruption (Wright R C, J Am Acad Dermatol, 49:160-1, 2003) and another with perforating folliculitis (Gilaberte Y et al., British J of Dermatol, 156:368-71, 2007) were reported. Two review studies (Leigh I M et al., Vlini Exp Dermatol, 10: 58-67, 1985; Schofield J K et al, Br J Dermatol, 128: 542-5, 1993) found that about 70% of recurrent erythema multi-forme were precipitated by HSV. A double-blind trial in 1995 (Tatnall F M, British J of Dermatology, 132:267-70 (1995)) shown that recurrent erythema multiforme can be completely suppressed by continuous acyclovir therapy. In this invention atopic dermatitis-like eruption was proved to be precipitated by HSV infection. These are further indirect evidences that HSV can cause systemic infection and manifests as dermatitis, erythema multiforme, acne and arthritis.

Consequently, the treatment in the present invention of acne may comprise a cream or an ointment mixed by an Anti-HSV agent to put on the affected part of the patient, wherein the Anti-HSV agent comprises Valacyclovir or Acyclovir. For example, the ADO ointment used in this invention contains acyclovir, lidocaine and diclofenac.

1st Clinical Case of Impetigo

Figure 23B:
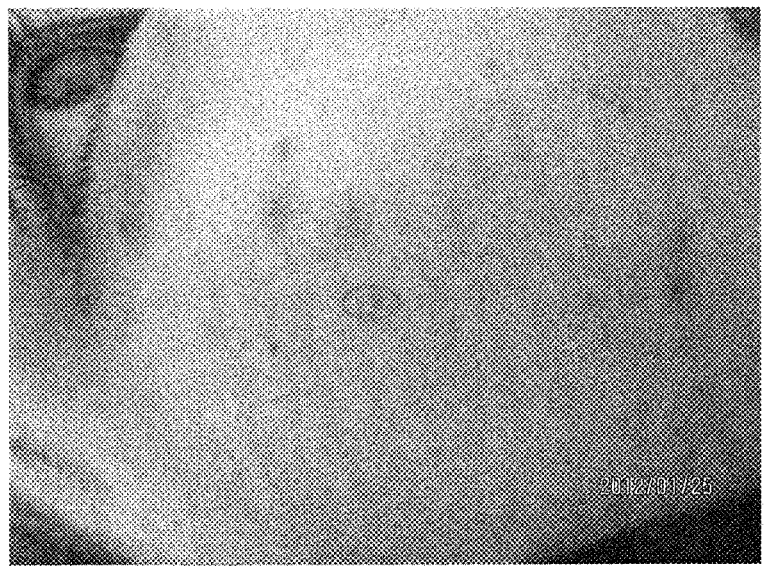
FIG. 23a-FIG. 23b are pictures showing $1^{st}$ clinical case of impetigo before treatment.
Figure 23A:
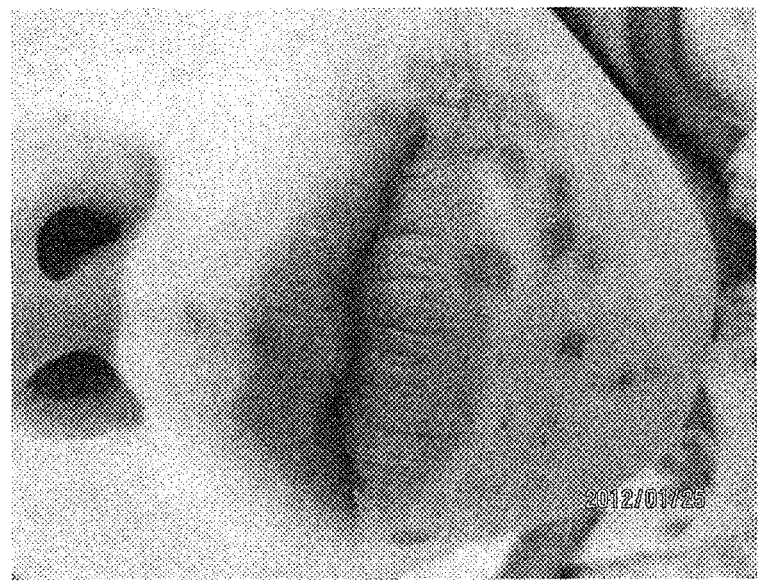

Before the treatment: FIG. 23a is a patient presented with increasing crusted vesicles appearing around her mouth for 1 week. Some vesicopapules were also found over her right cheek about 2 days ago.

Figure 24A:
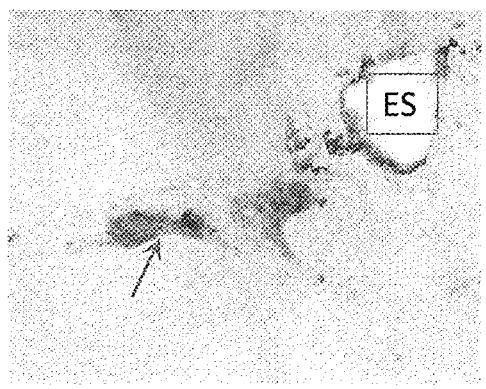
FIG. 24a-FIG. 24c are photomicrographs of cells of $1^{st}$ clinical case of impetigo.

Before the treatment: FIG. 23b Some vesicopapules were also found over her right cheek. A vesicle (circle) was removed for QTT FIG. 24a is a first image of QTT sample: The QTT taken from the vesicle over the cheek included an epidermal sheet (ES) and band-like dermal compartment. The DNFs (arrow) was surrounded by an inflammatory infiltration.

Figure 24B:
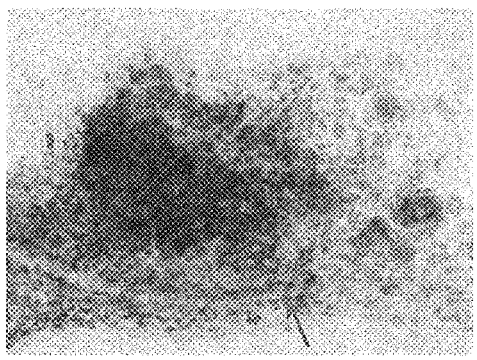

FIG. 24b is a second image of QTT sample: Balloon degeneration of the Schwann cells around a degenerated DNF (arrow). Some BCs gathered to become BC nests. EIBs were observed in some BCs.

Figure 24C:
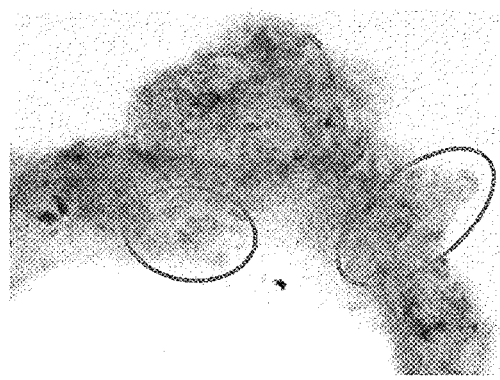

FIG. 24c is a third image of QTT sample: Micrococi (circles) was observed overlaid the BCs.

Figure 25:
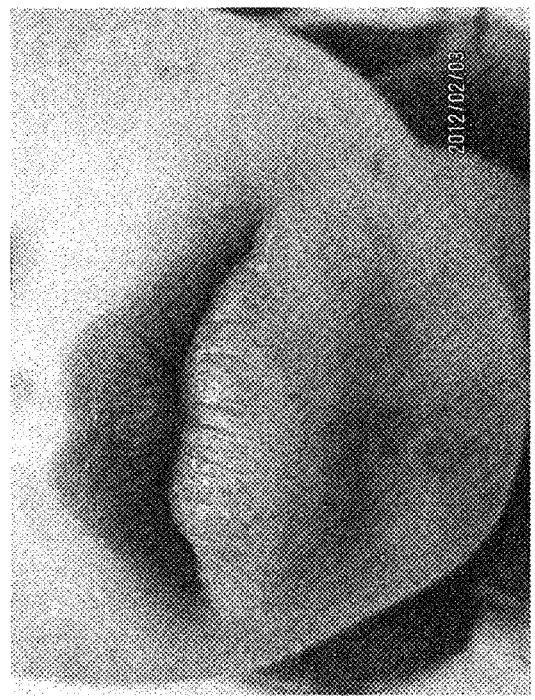
FIG. 25 is a picture showing $1^{st}$ clinical case of impetigo after treatment.

Diagnosis: impetigo induced by HSV infection
Prescriptions:
Acyclovir G. 10 mg/kg 4 times a day for 7 days (1st visit)
Oral antibiotics for 4 days (2nd visit)
Anti-allergic agents for 8 days
Antibiotics ointment After the treatment: FIG. 25 is an affected part of the patient after the treatment. After Acyclovir for 7 days, there were only some erythema on her mandible and some small red erosions over right cheek 9 days later. As micrococi were observed in the QTT, cefcapene pivoxil hydrochloride for 4 days was prescribed.

2nd Clinical Case of Impetigo

Figure 26:
FIG. 26 is a picture showing $2^{nd}$ clinical case of impetigo before treatment.

Before the treatment: FIG. 26 is a patient presented with many vesicopapules appearing over her mandible since 10 days ago. The vesicopapules dried and merged into a plaque with many yellowish crusts and surrounded by vesicopapules.

Figure 27A:
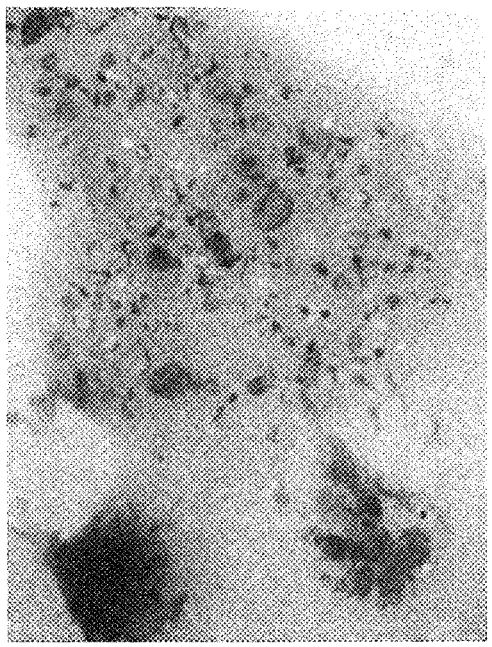
FIG. 27a-FIG. 27b are photomicrographs of cells of $2^{nd}$ clinical case of impetigo.

FIG. 27a is a first image of QTT sample: The QTT taken from the mandible revealed degenerated nerves surrounded by ballooning Schwann cells.

Figure 27B:
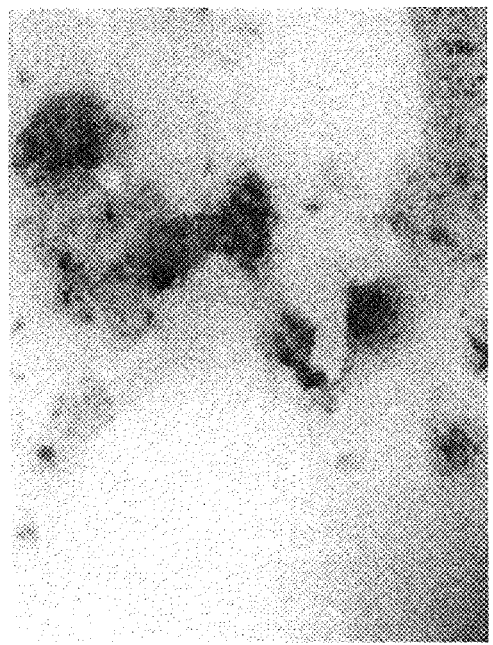

FIG. 27b is a second image of QTT sample: Many BCs and balloon cell nests (BCNs) with high N/C ratio were observed in the dermis.

Figure 28:
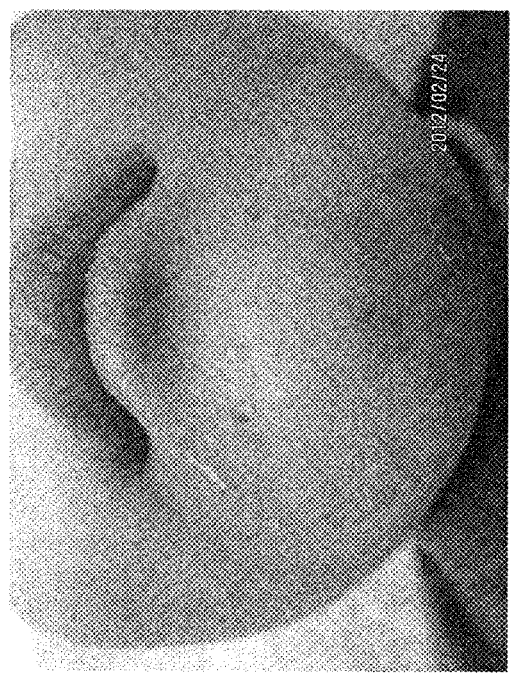
FIG. 28 is a picture showing $2^{nd}$ clinical case of impetigo after treatment.

Diagnosis: impetigo induced by HSV infection
Prescriptions:
Acyclovir G. 10 mg/kg 4 times a day for 7 days
Antibiotics ointment After the treatment: FIG. 28 is an affected part of the patient after the treatment. The lesion dried, desquamated and became flat 3 days later.

Figure 29:
FIG. 29 is a picture showing $3^{rd}$ clinical case of impetigo 3 days after the treatment.

3rd Clinical Case of Impetigo 3 days after the treatment: FIG. 29 is after the treatment the vesicles found over her left neck 6 days ago collapsed. Some vesicles over her face appeared on the day she came to clinic despite of the treatment.

Figure 30B:
FIG. 30a-FIG. 30b are photomicrographs of cells of $3^{rd}$ clinical case of impetigo.
Figure 30A:
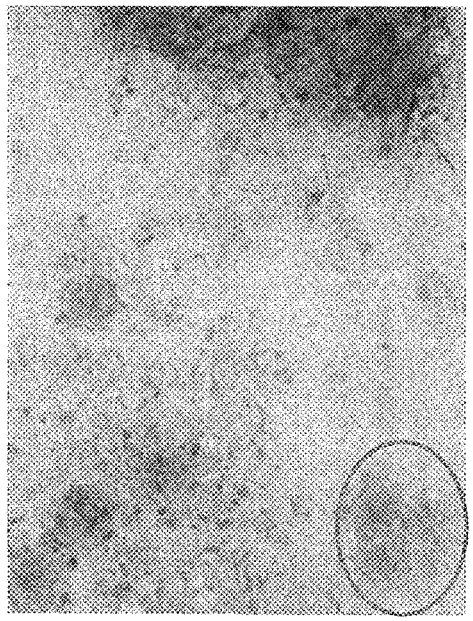

FIG. 30a is a first image of QTT sample: The QTT taken from a vesicle revealed BC with pleomorphic nuclei and high N/C ration gathering together to form a BC nest (circle). A degenerated nerve (arrow) was surrounded by ballooning Schwann cells.

FIG. 30b is a second image of QTT sample: The QTT taken from a vesicle revealed a lot of balloon cells and giant cell with severe nuclear pleomorphism.

Diagnosis: impetigo induced by HSV infection
Prescriptions:
Valacyclovir: 2 tablets daily for 7 days (1st visit)
Anti-allergic agent
Antibiotics 2 days due to cocci were also found on the QTT (2nd visit)

Figure 31:
FIG. 31 is a picture showing $3^{rd}$ clinical case of impetigo after treatment.

After the treatment: FIG. 31 is an affected part of the patient after the treatment. Symptoms have significantly improved 7 days later.

4th Clinical Case of Impetigo

Figure 32:
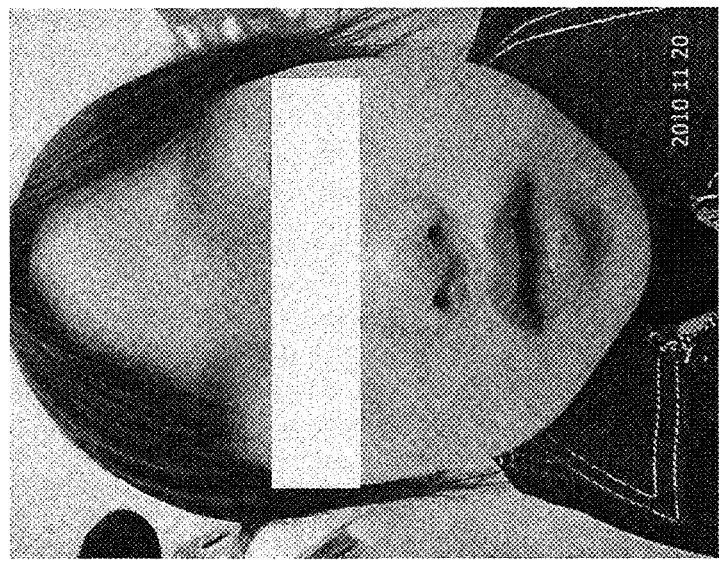
FIG. 32 is a picture showing $4^{th}$ clinical case of impetigo before treatment.

Before the treatment: FIG. 32 is a patient presented with large yellowish red crusts with exudation on her right nostril, mandible and left eye for 1 week.

Figure 33B:
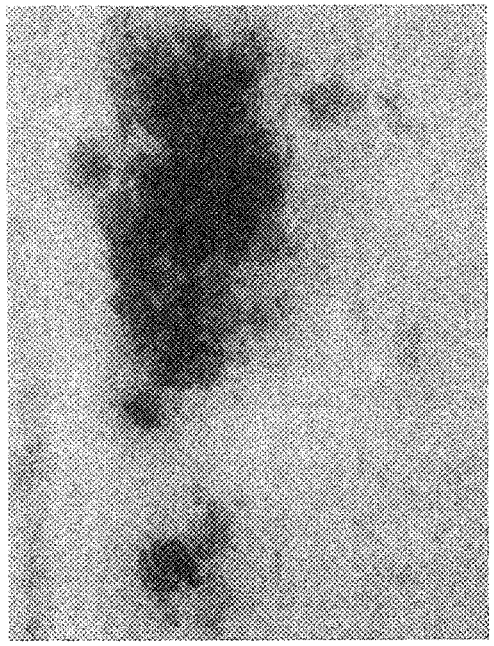
FIG. 33a-FIG. 33b are photomicrographs of cells of $4^{th}$ clinical case of impetigo.
Figure 33A:

FIG. 33a is a first image of QTT sample: The QTT taken from a vesicle on her left eye revealed balloon degeneration of the Schwann cells of a DNF. The DNF extends to the epidermal sheet (ES).

FIG. 33b is a second image of QTT sample: The QTT taken from a vesicle revealed many BCs and BCNs were observed in the dermis. The N/C ratio of the BC is very high.

Figure 34:
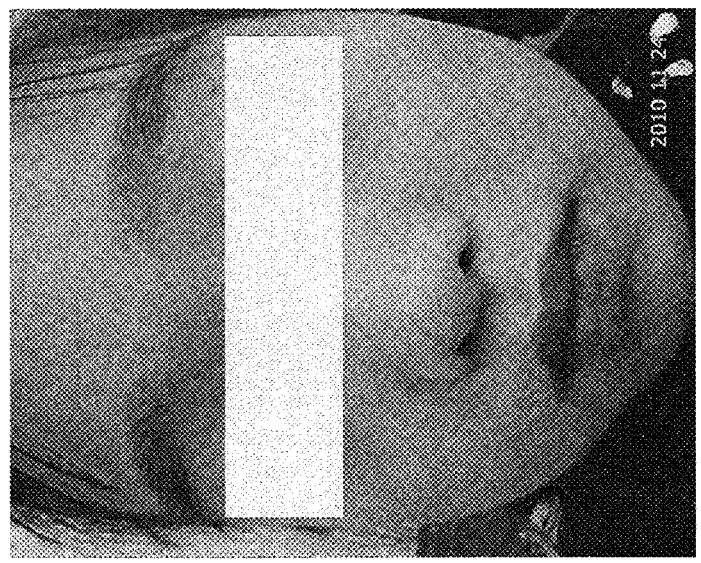
FIG. 34 is a picture showing $4^{th}$ clinical case of impetigo after treatment.

Diagnosis: impetigo induced by HSV infection
Prescriptions:
acyclovir G. 10 mg/kg 4 times a day for 7 days
Oral antibiotics and anti-allergic agent for 5 days
Antibiotics ointment After the treatment: FIG. 34 is an affected part of the patient after the treatment. There is nearly no skin lesion 4 days later. There is no recurrence till now (about one year).

5th Clinical Case of Impetigo

Figure 35:
FIG. 35 is a picture showing $5^{th}$ clinical case of impetigo before treatment.

Before the treatment: FIG. 35 is a patient presented with large yellowish red crusts in her nostrils and small ones over her face and complained of dry, scaly plaques over her trunk.

Figure 36:
FIG. 36 is a photomicrograph of cells of $5^{th}$ clinical case of impetigo.

FIG. 36 is an image of QTT sample: The QTT taken from a vesicopapule on her mandible revealed that the follicular epithelium in the dermis of a hair was completely destroyed. Loss of polarity, highly irregular nuclear contours were observed in the spinous layer.

Diagnosis: impetigo induced by HSV infection and auto-sensitization dermatitis

Figure 37:
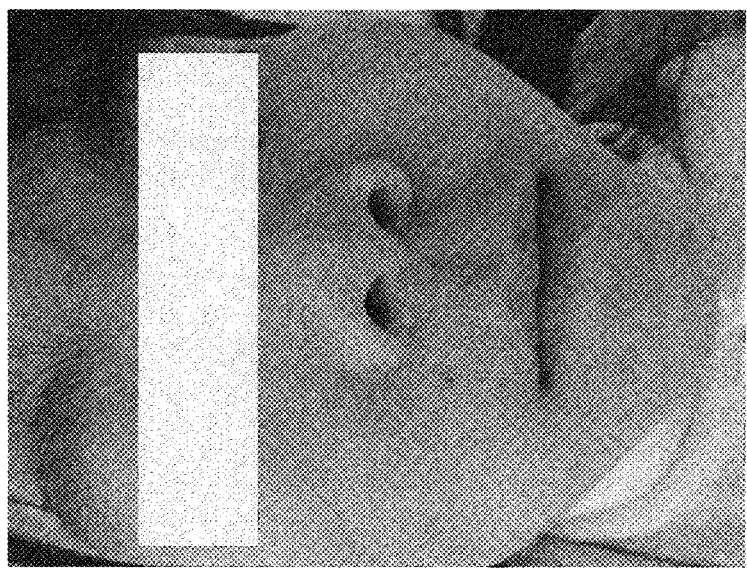
FIG. 37 is a picture showing $5^{th}$ clinical case of impetigo after treatment.

Prescriptions:
Acyclovir G. 10 mg/kg 4 times a day for 7 days
Anti-allergic agents for 17 days
Gr. IV topical corticosteroids
Antibiotic ointment After the treatment: FIG. 37 is an affected part of the patient after the treatment. There are some small erosions around her month and some vesiculopapules over the erythematous eyelids 5 days later. There is no recurrence till now (about 14 months).

The mobility of impetigo in children is high. The most severe complication is glomerulonephritis. Fortunately, Streptococci induced impetigo is now commonly treated with antibiotics, the post-streptococcal glomerulonephritis is a rare complication (Post-streptococcal glomerulonephritis-PubMed Health, (2011)). On the other hand, 94% of chronic glomerulonephritis patients had a diagnostically significant level of IgG class anti-herpetic antibodies (Barinskii I F et al. "Herpesvirus infection in patients with chronic glomerulonephritis" Vopr Virusol 50 (1):35-37 (2005)) was reported. Among 75 patients studied, HSV type 1 (34.4%), HSV type 2 (2.6%), cytomegalovirus (12%), mixed infections (46%). This result is consistent with this invention. The undiagnosed HSV (including other viruses)—induced impetigo may complicate by glomerulonephritis. In this invention, patients presented as impetigo diagnosed by the QTT responded well to the antiviral agent, thus the QTT may be a good screener to diagnose the HSV induced impetigo. Consequently, decrease the incidence of chronic glomerulonephritis.

1st Clinical Case of Pyoderma Gangrenosum

Figure 38:
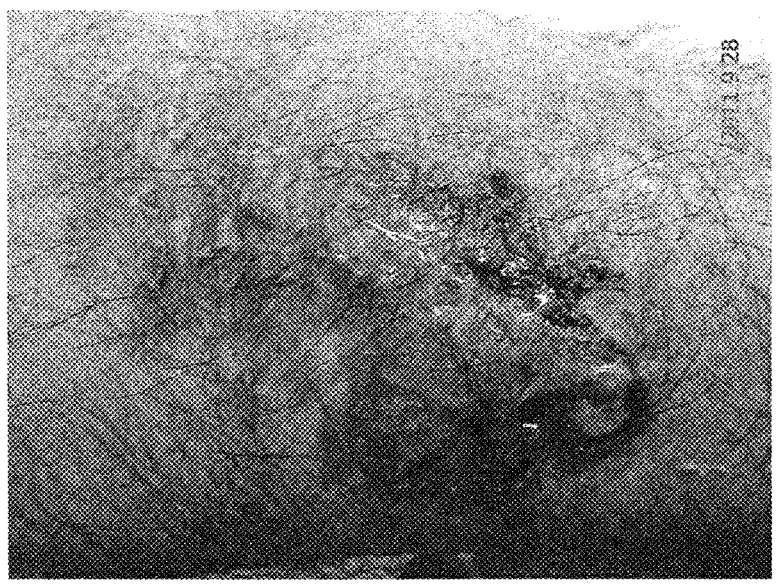
FIG. 38 is a picture showing $1^{st}$ clinical case of pyoderma gangrenosum before treatment.

Before the treatment: FIG. 38 is a patient presented with a large ulcer with yellowish exudation on the anterior aspect and a large crusted plaque on the posterior aspect of his lower leg. Besides, nearly half of the skin was reddish and edematous.

Figure 39:
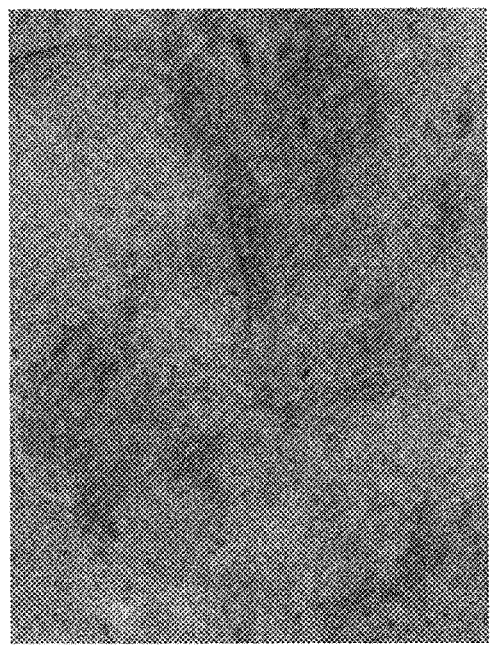
FIG. 39 is a photomicrograph of cells of $1^{st}$ clinical case of pyoderma gangrenosum.

FIG. 39 is an image of QTT sample: A degenerated nerve was surrounded by many pleomorphic BCs. Melanin pigments were also observed.

Laboratory data:
HSV IgG enzyme immunoassay titer (normal <2.0): >128
CMV IgG enzyme immunoassay titer (normal <2.0): 4.5
*Staph. Aureus* (MRSA): +
Diagnosis: pyoderma gangrenosum induced by HSV infection
Prescriptions:
Valacyclovir: 3 tablets daily for 10 days
Anti-allergic agent for 10 days
Antibiotics ointment
Gr. III topical corticosteroids (CS)

Figure 40:
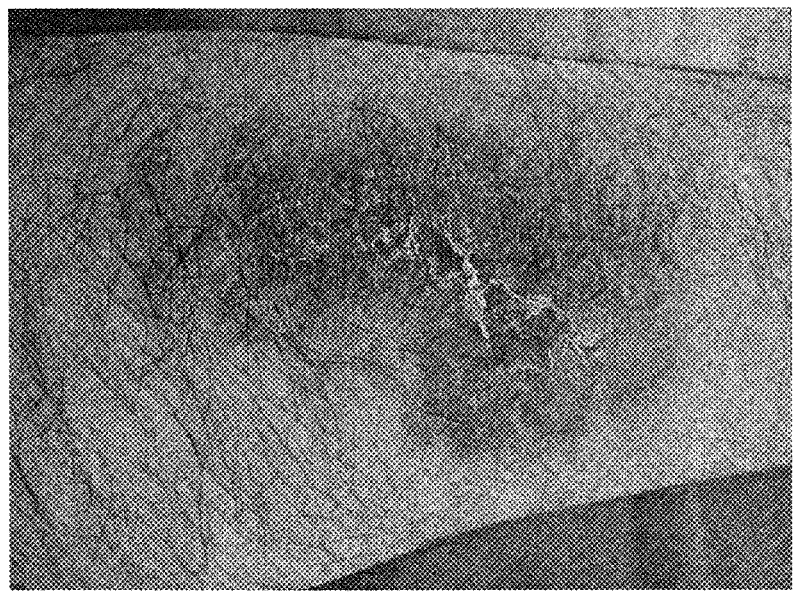
FIG. 40 is a picture showing $1^{st}$ clinical case of pyoderma gangrenosum after treatment.

After the treatment: FIG. 40 is an affected part of the patient after the treatment. 10 days later, although reddish-brown plaques were left, there were no more erosions and oozing.

2nd Clinical Case of Pyoderma Gangrenosum

Figure 41:
FIG. 41 is a picture showing $2^{nd}$ clinical case of pyoderma gangrenosum before treatment.
Figure 41:
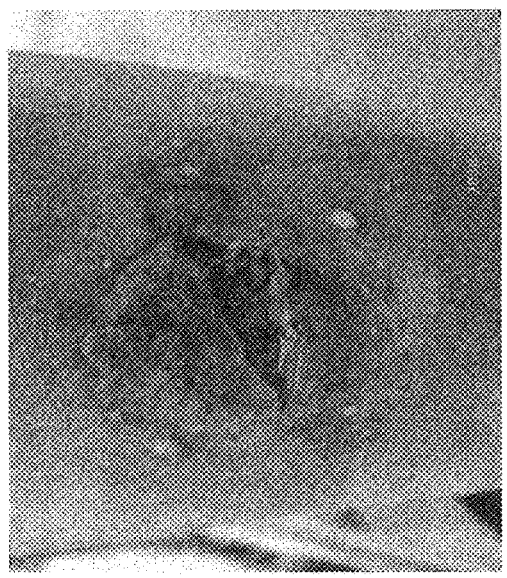

Before the treatment: FIG. 41 is a patient treated with systemic corticosteroids due to ulcerative colitis diagnosed 2 years ago. Several pustules appeared on her both legs 10 days ago. Some enlarged very fast and became nodules.

Figure 42:
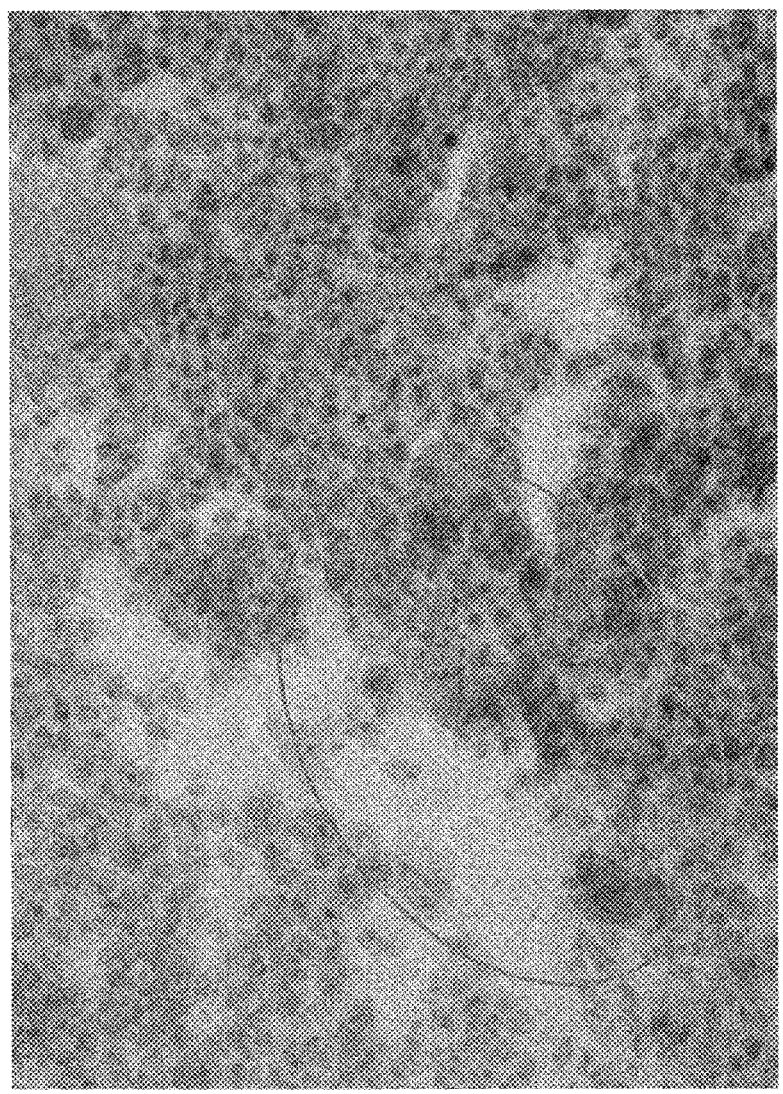
FIG. 42 is a photomicrograph of cells of $2^{nd}$ clinical case of pyoderma gangrenosum.

FIG. 42 is an image of QTT sample: The QTT from a pustules revealed many BCs with eosinophilic inclusion body were seen among a dense inflammatory infiltration mainly by polymorphonuclear leukocytes. Degenerated nerves (arrow) were observed in the right upper corner. BCs with eosinophilic inclusion bodies in their nuclei (circle) were observed.

Figure 43:
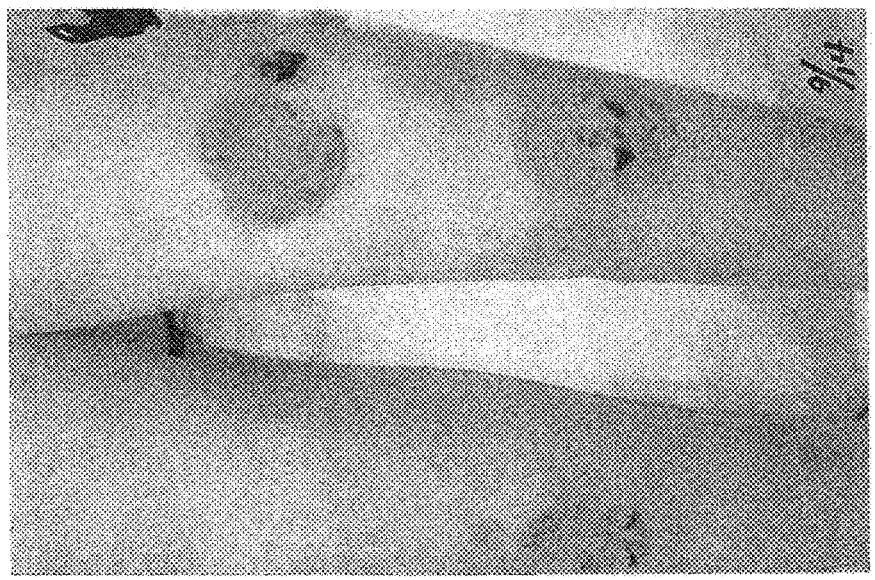
FIG. 43 is a picture showing $2^{nd}$ clinical case of pyoderma gangrenosum after treatment.

Diagnosis: pyoderma gangrenosum induced by HSV infection
Prescriptions:
1. oral prednisolone 40 mg for 11 days, then decreased to 35 mg, 30 mg, 30 mg, 25 every 7 days. The dose was further decreased and maintained dose was 15 mg.
2. Antibiotic ointment: gentamycin
3. Other treatment for ulcerative colitis is mesalazine After the treatment: FIG. 43 is an affected part of the patient after the treatment. Symptoms have significantly improved after the treatments. Some nodules healed and there were only some large erosions left 13 days later.

Viral infection has been implicated as precipitating factor of ulcerative colitis. However, only few papers succeeded in viral culture, the treatment are immunosuppressant agents to control the symptoms. It was reported that 0.6-5% of patients (Greenstein A J, "The extra-intestinal complications of Crohn's disease and ulcerative colitis", *Medicine* 55: 401-412 (1976)) suffering from ulcerative colitis complicated by pyoderma gangrenosum. Total proctocolectomy for extensive chronic ulcerative colitis was reported to bring about healing of associated pyoderma gangrenosum and without recurrence (Powell F C et al., *Arch Dermatol*, 120: 757-61, (1984)). This report confirmed that similar histopathological change may occur both in the gastrointestinal tract and skin. These 2 patients were diagnosed by the QTT as HSV infection. The first patient was treated by antiviral agent satisfactorily. It is worthwhile to apply The QTT to detect if there is a similar histopathological change in the gastrointestinal tract as found in the skin of the 2nd patient.

On the other hand, there are many reports concerning the adverse cutaneous reaction secondary to treatment with tumor necrosis factors-alpha inhibitors after 2000. Eczematide-like purpura (Wang L C et al., *J Am Acad Dermatol*, 49:157-8, 2003) leucocytoclastic vasculitis (Devos S A et al., *Dermatology*, 206: 388-90, 2003; Mcllwain L et al., *J Clin Gastroenterol*, 36: 411-13, 2003) and psoriasiform eruption (Verea M M et al., *Ann Phamacother*, 38:54-7, 2004) were reported after administration of the tumor necrosis factors—alpha inhibitors in patients suffering with Crohn's disease. These adverse reactions may occur with the same mechanism as in the patient 2nd clinical case of pyoderma gangrenosum with ulcerative colitis. It represents a systemic and peripheral spreading of the diseases. In other words, the adverse reaction actually provides a good chance for the QTT to detect their underlying etiology.

Pyoderma gangrenosum may complicate another important and mysterious disease: myelodysplasia. Nonmyelinating Schwann cells ensheathed autonomic nerves in mouse bone marrow was proved responsible for activation of the hematopoietic cells. Autonomic nerve denervation induced rapid loss of hematopoietic cells (Yamazaki S et al., *Cell*, 147:1146-58, 2011). In this invention, QTT detects the degenerated dermal nerve fibers surrounded by ballooning Schwann cells in various cutaneous diseases. Consistent with this latest reports, degenerated ballooning Schwann cells induce dysfunction of peripheral nerves thus bring vesicles, pustules, erosions and ulcers in skin; and bone marrow dysplasia (myelodysplasia) respectively. This can be applied to many other diseases associated with pyoderma gangrenosum. The frequent associations are rheumatoid arthritis (Stolman et al., *Arch Dermatol*, 111:1020-3 (1975)), Felty's syndrome (Kramer N et al., *J Rheumatol*, 17: 1079-82 (1990)), osteoarthritis (Lazarus G S et al., *Arch Dermatol*, 105:46-51 (1972)), acne conglobata (Powell F C et al., *Q J Med*, 55: 173-86 (1985)) and sacroileitis (Holt P J A et al., *Medicine* (Baltimore) 59: 114-33 (1980)). In this invention, QTT can thus be useful in elucidating weather these associated diseases are actually systemic infection of HSV.

1st Clinical Case of Chilblain

Figure 44:
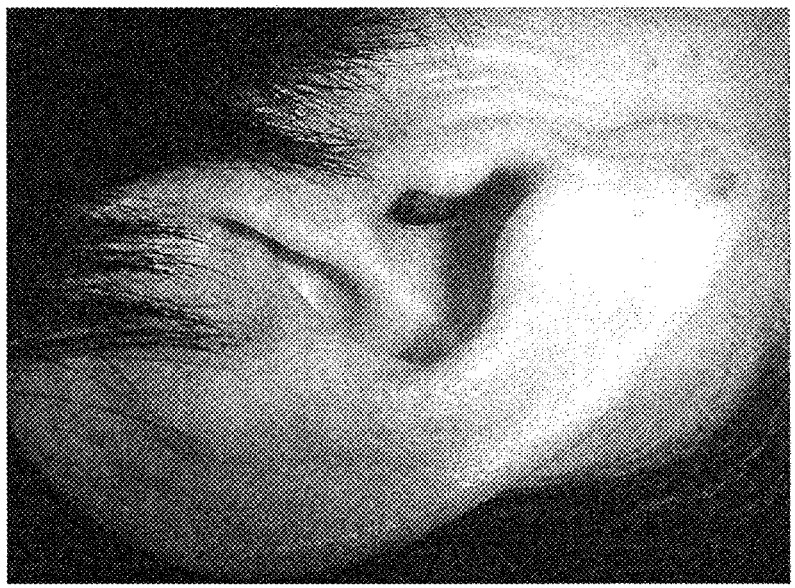
FIG. 44 is a picture showing $1^{st}$ clinical case of chilblain before treatment.

Before the treatment: FIG. 44 is a patient presented erythematous swellings of her both ears for one week. There are erosions over her right earlobe.

Figure 45A:
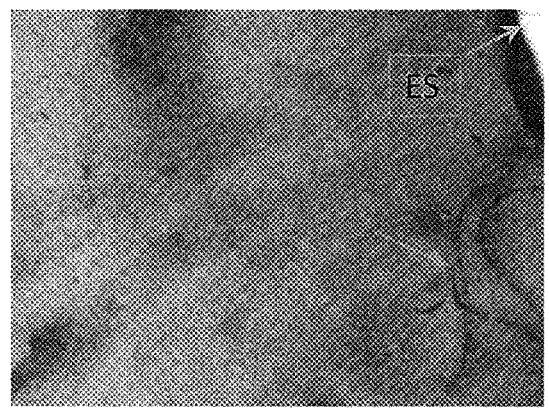
FIG. 45a-FIG. 45c are photomicrographs of cells of $1^{st}$ clinical case of chilblain.

FIG. 45a is an image of QTT sample: There were several bands composed by inflammatory infiltration and degenerated tissues observed in the dermis. Several DNFs (arrow) extended from deep dermis to epidermal sheet (ES).

Figure 45B:
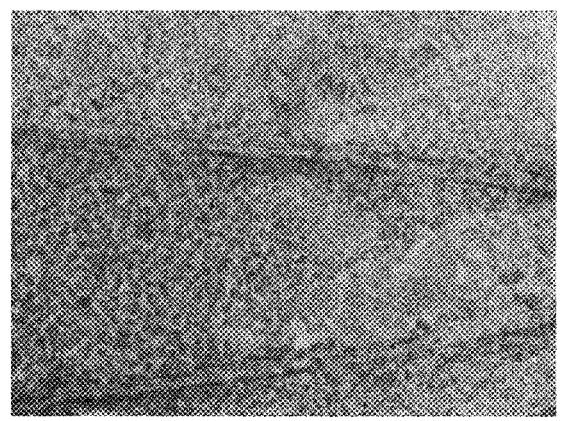

FIG. 45b is an image of QTT sample: A giant cell and some ballooning Schwann cells with pleomorphic nuclei were seen between 2 DNFs.

Figure 45C:
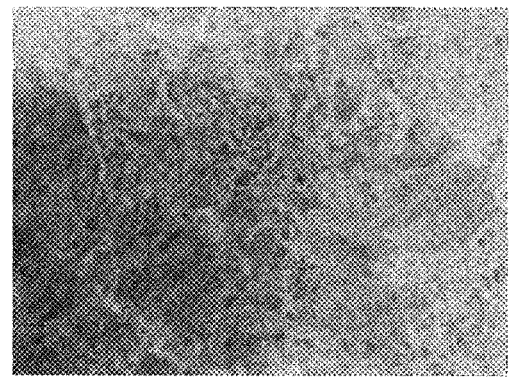

FIG. 45c is an image of QTT sample: Fine nerve fibers surrounded by ballooning Schwann cells were observed in deep dermis.

Figure 46:
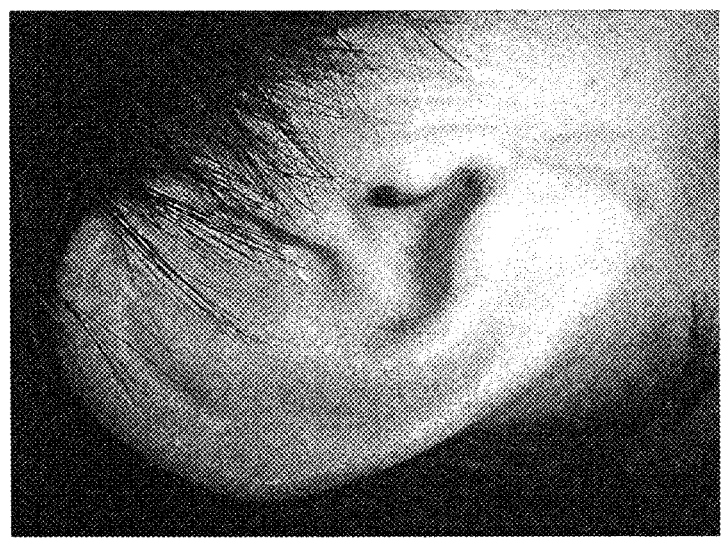
FIG. 46 is a picture showing $1^{st}$ clinical case of chilblain after treatment.

Laboratory data:
Non-specific immunoglobulin E (Ig E) titer (normal <170 IU/ml): 7.9 IU/ml
HSV IgG (normal <2.0): 39.3
CMV IgG (normal <2.0): 33.7
Prescriptions:
Acyclovir 200 mg: 3 tablets daily for 7 days
Diagnosis: chilblain induced by HSV infection
After the treatment: FIG. 46 is an affected part of the patient after the treatment. The swelling and pain decreased a lot. The erosion improved 7 days later.

Figure 47:
FIG. 47 is a picture showing $2^{nd}$ clinical case of chilblain 4 days after treatment.

2nd Clinical Case of Chilblain 4 days after 1st prescriptions: FIG. 47 is a patient presented red swollen fingers with pain for one month. The lesions exacerbated gradually. The patient was treated yet without effect. This picture was taken 4 days after 1$^{st}$ prescriptions under the diagnosis of HSV infection base on QTT and laboratory data.

Figure 48:
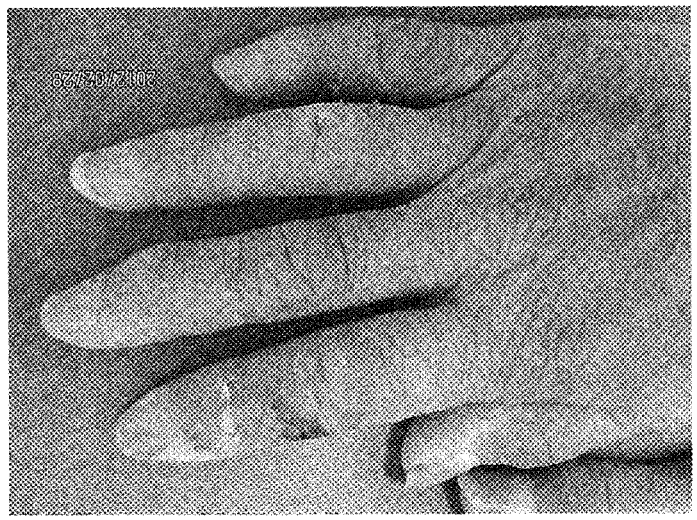
FIG. 48 is a picture showing $2^{nd}$ clinical case of chilblain after $2^{nd}$ prescriptions.

Laboratory data:
HSV IgG (normal <2.0): 33.8
Diagnosis: chilblain induced by HSV infection
Prescriptions of 1$^{st}$ step:
Valacyclovir: 2 tablets daily for 4 days
Tocophenol nicotinate for 4 days
Anti-allergic agent for 4 days
Gr. III topical corticosteroids over the itchy lesions of the patient
Prescriptions of 2$^{nd}$ step:
Valacyclovir: 1 tablets daily for 14 days
Anti-allergic agent for 14 days
ADO ointment: 2 time daily After the treatment of 2$^{nd}$ prescriptions: FIG. 48 is an affected part of the patient after the treatment of 2$^{nd}$ prescriptions. The red swollen fingers with pain were improved.

Figure 49:
FIG. 49 is a picture $2^{nd}$ clinical case of chilblain after $3^{rd}$ prescriptions.

Prescriptions of 3$^{rd}$ step:
Valacyclovir: 1 tablets daily for 14 days
Anti-allergic agent for 14 days
ADO ointment: 2 time daily After the treatment of 3$^{rd}$ prescriptions: FIG. 49 is an affected part of the patient after the treatment of 3$^{rd}$ prescriptions. The red swollen fingers with pain were nearly cured.

Chilblain is localized inflammatory lesions that are caused by continued exposure to cold and dampness. Characteristic locations include the fingers, toes, heels, nose and ears. Nifedipine has been reported to be benefit (Down P M et al. "Nifedipine in the treatment of chilblains" *Br Med J*, 293: 923 (1986)), yet may induce headache and flushing. Cortisone ointment for itching and antibiotics for prevention of secondary infection are the most popular remedies. To the best of our knowledge, this invention includes the first description of the histopathological features of the HSV infection inducing DNF changes in chilblains by the QTT. Cold exposure induces replication of the latent HSV in DNFs and nerve free endings (NFEs). In addition, evokes a substance P mediated neurogenic inflammation presented as chilblain. The prompt response to the antiviral agents was consistent with the high titer of the HSV IgG which was 39.3. Another 8 patients cured by various amounts of antiviral agents are included in this invention. Besides 2 children not checked, the titer of the HS Ig G patients suffered from chilblains was 33.8 to over 128.

| Sex | Age | body parts | HSV IgG | Acyclovir 200 mg | Acyclovir 400 mg | Valacyclovir 500 mg |
|---|---|---|---|---|---|---|
| female | 82 | feet | 76.7 | 25 T | 50 T | |
| male | 74 | feet | 108 | 25 T | | |
| male | 58 | feet | 107 | 25 T | | 27 T |
| female | 11 | hands | | 25 T | | |
| female | 10 | feet | | 25 T | | |
| female | 88 | feet | >128 | 50 T | | |
| male | 77 | hands | 107 | 25 T | | 17 T |
| male | 68 | feet | >128 | 25 T | 30 T | |

Although chilblains is a self-limited disease, it is included in the diagnostic criteria of the systemic lupus erythematous (SLE). Viguier M. et al. investigated 33 patients affected with chilblain lesions for more than 1 month (Viguier M. et al., "Clinical and histopathologic features and immunologic variables in patients with severe chilblains. A study of the relationship to lupus erythematous" *Medicine* (Baltimore) 80 (3): 180-188 (2001)). 22 patients showed one or several abnormalities for the connective tissue diseases and 8 had a diagnosis of SLE. The hitopathologic studies included revealed only a deep perisudoral inflammatory infiltration. As there are many autonomic nerves around eccrine glands, the infiltration may represent the substance P mediated neurogenic inflammatory reaction toward HSV-infected cells.

Viral infection may cause death of the infected cells by direct effect. However, the HSV belonging to DNA viruses tend to integrating themselves in the cell nuclei where they produce latent infection (Young B et al., *Wheater's Basic Pathology*, 44 (2011)). Consequently, the genome of the host cell is recognized as foreign. This process may trigger the immune system to produce antibodies against the changed self to induce autoimmune hepatitis A (Vento S et al., *Autoimmunity Reviews*, 3:61-69 (2003)). In other words, auto antibodies detected in autoimmune diseases is the process in order to eradicate the viral-infected cells and not necessarily harmful. The inflammatory reaction in SLE may as in the chilblains aroused by the HSV infected Schwann cells in various organs and systems. Besides chilblain, glomerulonephritis, arthritis, anemia, cytopenia those among the diagnostic criteria of the SLE are included in this invention.

Although the clinical symptoms and sighs of the peripheral neuropathy are thoroughly described, a specific cause cannot be identified. The nerve damage provoked after viral and bacterial infection was referred to as an indirect autoimmune processes as in SLE. This may be due to the HSV-infected cells do not show up in traditional thin HE and other stains. Besides chilblain, these phenomena may occur in diabetes mellitus (DM), Guillain-Barre syndrome, multiple sclerosis and chronic inflammatory demyelinating polyneuropathy. QTT or a thick Giemsa cytologic observation may be a better tool than traditional ones.

Clinical Case of Diabetic Skin Complications

Figure 50:
FIG. 50 is a picture showing the clinical case of psoriasiform before treatment.

Before the treatment: FIG. 50 is a patient presented many scaly reddish papules of various sizes and some psoriasiform plaques appeared over lower legs for one month. The scaly reddish papules of various sizes and some psoriasiform plaques were not itchy.

Figure 51:
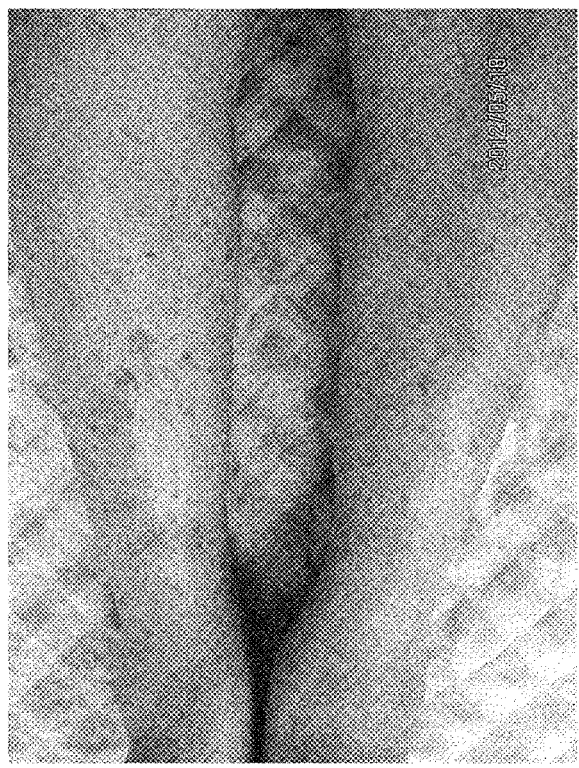
FIG. 51 is a picture showing the clinical case of psoriasiform after treatment.

Laboratory data:
Ig E (normal <170 IU/ml): 12.8 IU/ml
HSV IgG enzyme immunoassay titer (normal <2.0): >128
CMV IgG enzyme immunoassay titer (normal <2.0): 111
Diagnosis: psoriasiform plaques induced by HSV infection
Prescriptions:
Narrowband Ultraviolet light B (NBUVB)
Gr. I and III topical corticosteroids (CS)
Acyclovir (400 mg): 3 tablets daily for 10 days continued by 2 tablets daily for another 10 days After the treatment: FIG. 51 is an affected part of the patient after the treatment. Some lesions disappeared and the scaling of the psoriasiform plaques decreased a lot 7 days afterwards.

About 60% to 70% of people with DM have mild to severe form of nerve system damage. On the same time, skin problems are common. 22 patients were treated due to various kinds of diabetic skin complications. The titer of the HSV IgG or CMV IgG of the patients listed below was high, they all responded well after adding antiviral agents into traditional treatments of the skin diseases.

| Sex | Age | HSV IgG CMV IgG | IgE | skin manifestation |
|---|---|---|---|---|
| male | 73 | 48.8 | 26.4 | psoriasiform |
| male | 55 | | | pyoderma |
| male | 62 | 41.9 | 1,625 | burn ulcer |
| male | 68 | <2.0 9.9 | 318 | dermatitis, tinea ungium |
| male | 67 | 45.4 11.8 | 57.1 | urticaria |
| male | 77 | >128 | | tinea ungium |
| male | 76 | | | psoriasiform |
| male | 64 | <2.0 21.7 | | autosensitization dermatitis |
| male | 62 | <2.0 30.2 | 37.7 | nummular eczema verruca vulgaris |
| male | 77 | >128 | 6.2 | psoriasiform |
| male | 64 | 74.6 22.1 | 346 | autosensitization dermatitis |
| male | 56 | >128 | 163 | Kaposi's variceliform eruption |
| male | 79 | 65 | 82.6 | nummular eczema |
| male | 47 | 37 | 183 | pemphigus foliaceous |
| female | 69 | 5.2 | 264 | acute urticaria |
| female | 83 | 6.5 | 7.4 | Kaposi's variceliform eruption |
| female | 70 | >128 | 14.5 | chronic urticaria |
| female | 74 | 69.4 | 15.8 | autosensitization dermatitis |
| female | 65 | >128 111 | 12.8 | psoriasiform |
| female | 78 | 104 | 61.6 | Kaposi's variceliform eruption |
| female | 49 | 89.9 25.2 | 247 | chronic ulcer |
| female | 73 | 70 | 255 | acne-like |

In 1976 Brown et al. found that enhanced glycogenic effects of neurotension and substance P over glucagon may result from their inhibition of insulin release (Brown et al., *Endocrinology,* 98:819-22 (1976)). It is reasonable to speculate that if the autonomic nerve controlling insulin secretion is infected by the HSV just as shown in this invention in the cases of chilblain would result in substance P secretion and consequent inhibition of insulin release. DM complicated by polyneuropathy had marked reduction of Substance P and calcitonin-related peptide containing nerve fibers in the dermis (Lindberge M et al., *J of Neruological Science,* 93: 289-296 (1989)) may be the result of the destruction of the DNFs. In a review article, O'connor T M et al. provided evidences proving that many chronic inflammatory diseases such as asthma, sarcoidosis, chronic bronchitis, IBD and RA are due to elevated level of the Substance P (O'connor T M et al., *J cellular physiology,* 201 167-180 (2004)).

The nerve network of the skin contains somatic sensory and sympathetic autonomic fibers. They function at every point of the body. Sensory nerve of the skin have been found to synthesize and release calcitonin gene-related peptide, somatostatin, substance P, neurokinin A, vasoactive intestinal peptide and melanocyte stimulating hormones (Karanth S et al., *Am J Anat* 191: 379 (1991)). The most important neuropeptide is substance P that was reported to be released in joint activating rheumatoid synoviocytes (Martin et al., Science, 235: 893-895 (1987)). The somatic peripheral nervous systems is responsible as receptors of touch, pain, temperature, itch and mechanical stimuli, and the automatic peripheral nervous systems control and regulate the body internally. If some parts of the peripheral nervous system is infected and become latent by the HSV, acute and chronic inflammation may be induced as observed in skin.

1$^{St}$ Clinical Case of Alopecia

Figure 52:
FIG. 52 is a picture showing 1$^{st}$ clinical case of alopecia before treatment.
Figure 52:
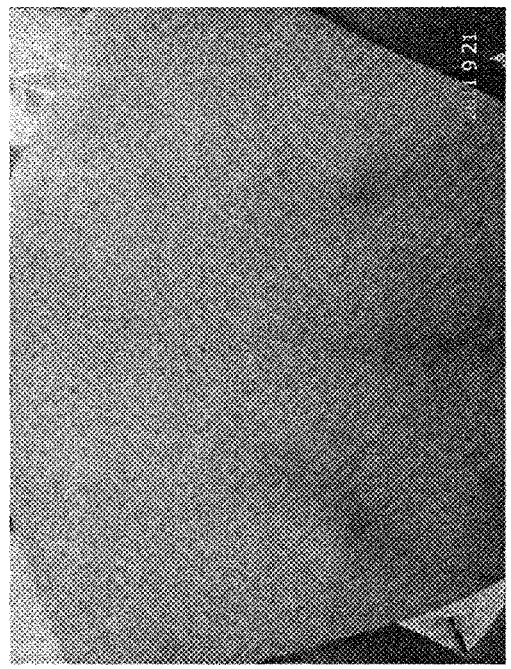

Before the treatment: FIG. 52 is a patient presented with recurrent itchy red vesicopapules over his back for 5 years. The patient also noticed a hair loss plaque over the right side of his scalp one week ago.

Figure 53A:
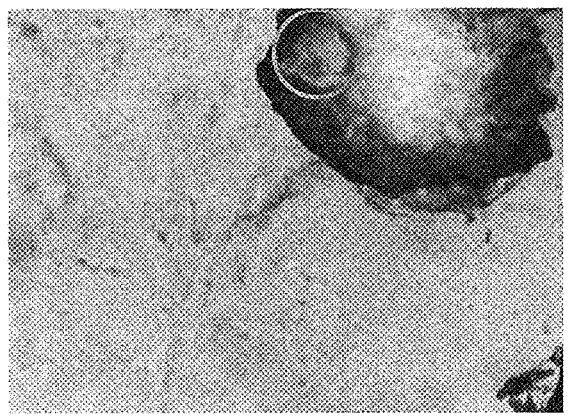
FIG. 53a-FIG. 53c are photomicrographs of cells of 1$^{st}$ clinical case of alopecia.

FIG. 53*a* is an image of QTT sample which from a red vesicopapule on the hair loss plaque revealed a large hair orifice (circle) filled by balloon cells.

Figure 53B:
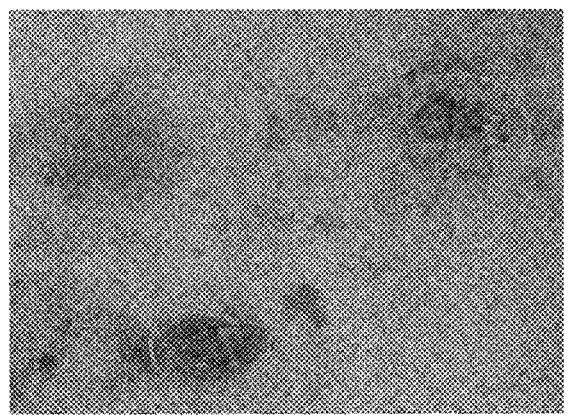

FIG. 53*b* is an image of QTT sample revealing a balloon degeneration of the Schwann cells of 2 dermal nerves (circles). The endoneurium (arrow) was partially preserved.

Figure 53C:
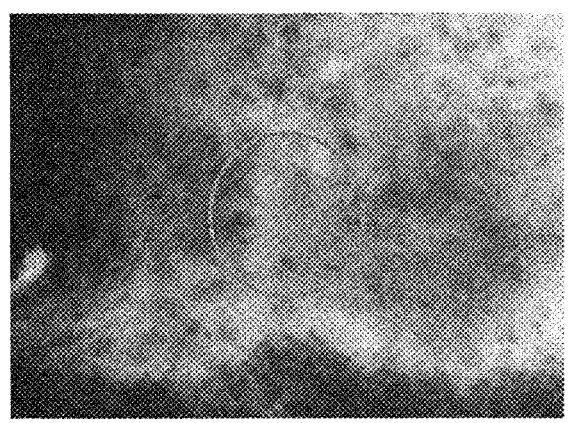

FIG. 53*c* is an image of QTT sample with high magnification revealed BCs and BCNs. BCs with EIBs (circle) were also found in the follicular orifice.

Diagnosis: alopecia and acne-like eruption due to HSV infection

Prescriptions:

Acyclovir (400 mg): 3 tablets daily for 10 days and 2 tablets daily for 14 days

Anti-allergic agent for 24 days

Gr. III topical CS.

Figure 54B:
FIG. 54a-FIG. 54d are pictures showing the 1$^{st}$ clinical case of alopecia after treatment.
Figure 54A:
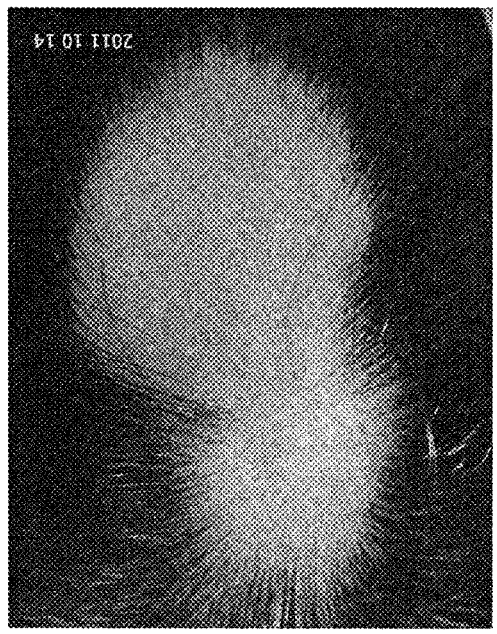

After the treatment:

FIG. 54*a* is an affected part of the patient after the treatment. Small white hairs appeared especially over central portion 23 days later.

FIG. 54*b* was taken about 7 weeks after he finished Valacyclovir 2 tablets daily for 5 days. New hairs including black hairs increased a lot.

Figure 54C:

FIG. 54*c* was taken 21 weeks later. During these 3 weeks except Valacyclovir 2 tablets daily followed by 1 tablets daily for 5 days and a VD cream was prescribed twice a day, wherein the VD cream contain Diclofenac and Lidocaine.

Figure 54D:
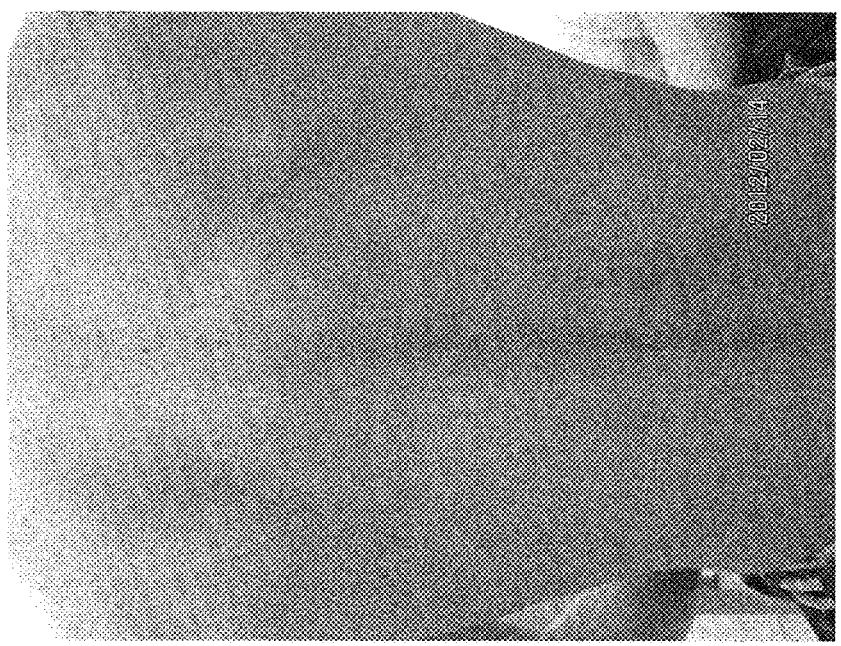

FIG. 54*d* is an affected part of the patient after the treatment. There are only a few vesicopapules and pustules on his back.

2$^{nd}$ Clinical Case of Alopecia

Figure 55A:
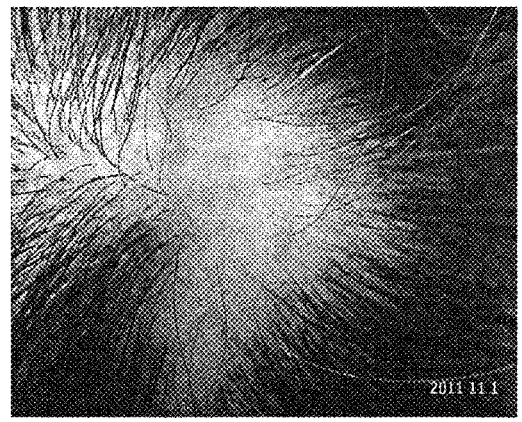
FIG. 55a-FIG. 55c are pictures showing 2$^{nd}$ clinical case of alopecia before treatment.
Figure 55B:
Figure 55C:

Before the treatment: FIG. 55*a* is a patient presented with a pustule appeared around a hair follicle over an atrophic whitish plague without hair appeared 4 years ago. Please refer FIG. 55*b*-55*c*, the patient also complained of hair loss especially over the posterior (FIG. 55*b*) and right (FIG. 55*c*) portions of her scalp.

Figure 56B:
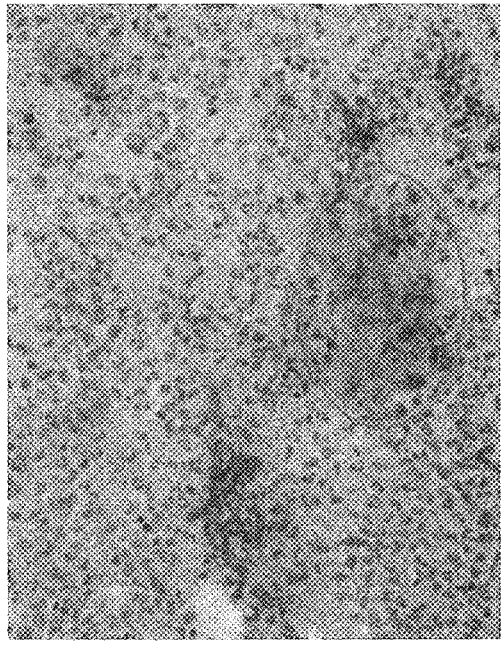
FIG. 56a-FIG. 56b are photomicrographs of cells of 2$^{nd}$ clinical case of alopecia.
Figure 56A:

FIG. 56*a* is an image of QTT sample which from the pustule. A degenerated nerve was surrounded by BCs (arrows), mononuclear cells, and many PMNs.

FIG. 56*b* is an image of QTT sample revealing a balloon cell island (circle) composed by BCs with pleomorphic nuclei was surrounded by an inflammatory infiltration mainly by PMNs.

Laboratory data:

HSV IgG enzyme immunoassay titer (normal <2.0): 45.1

Diagnosis: alopecia due to HSV infection

Prescriptions:

Valacyclovir 1 tablets daily after dinner for 95 days.

Anti-allergic agent for 15 days

Acyclovir ointment for 6 weeks

Figure 57A:
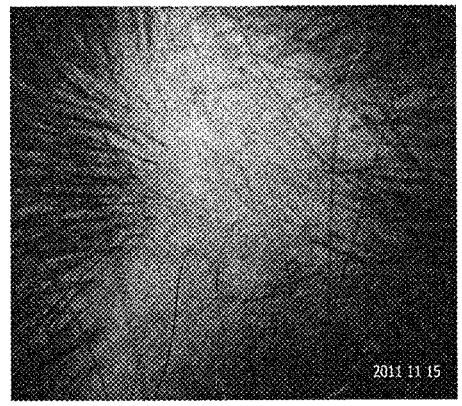
FIG. 57a-FIG. 57c are pictures showing the 2$^{nd}$ clinical case of alopecia after treatment.
Figure 57B:
Figure 57C:

After the treatment: FIG. 57*a* is an affected part of the patient after the treatment. The pustule disappeared a week later. There is nearly no change on the atrophic plague 2 weeks later. FIG. 57*b*, hair increased obviously on the right side and posterior aspect 4 weeks later. FIG. 57*c*, New black hairs (circle) were observed and no more alopecia on the right side 16 weeks later.

Alopecia (areata, universalis, cicatrica) is known as an autoimmune disease till now. Spontaneous recovery can be expected within a few months to a year in minor disease. Both of the patients suffered from alopecia have another disease acne-like eruption (1$^{st}$ case); vesicles around pelvic area (2$^{nd}$ case) caused by HSV.

Alopecia is usually presented as a hair loss area. The vesicopapule and pustule in the lesion provided a good chance for approaching the pathogenesis of alopecia. QTT from the vesicopapule and pustule confirmed that hair loss is due to the HSV infection of the Schwann cells in the DNFs. The degenerated nerve fibers were surrounded by the BCs and severe inflammatory infiltration. It is possible that the traditional histopathologic study only revealed the severe inflammatory infiltration and failed in disclosing the HSV-infected cells.

The patient in $2^{nd}$ case had a fibrotic alopecic plague for 4 years. Pustules appeared after the antiviral therapy suggested that the HSV infected cells were deeper in the dermis than that in the 1st case. The pustule is the result of the reaction after antiviral therapy. It took 4 months, but two patients had satisfactory recovery.

Alopecia is also included in the diagnostic criteria of the SLE besides chilblain, glomerulonephritis, arthritis, anemia, cytopenia. It is also common in autoimmune diseases such as acquired thyroid disease, vitiligo, diabetes and collagen diseases. There is a great chance that the inflammatory reaction toward changed self in these diseases may as in the alopecia aroused by the HSV infected Schwann cells in various organs and systems.

Other diseases are related to latent infection of the HSV in Peripheral nerve fibers (PNFs), dermal nerve fibers (DNFs) and free nerve endings (FNEs) besides above diseases. QTT enables cytology observation of the pathologic changes for the following diseases occurring in DNFs and FNEs of the epidermis and dermal nerve networks. The above mentioned anti-HSV agent or the combination thereof can be used for the treatment of the following other diseases, which are named as below:

Asteatotic dermatitis
  Ichthyosis
  Lichen simplex chronicus (Neurodermatitis, Prurigo)
  Seborrhoeic dermatitis
  Rosacea
  Perioral dermatitis
  Epidermal cyst
  Ulcerative colitis
  Crohn's disease
  Myelodysplasia, multiple myeloma
  Wound, ulcer
  Discoid lupus erythematosus
  Vitiligo
  Chilbrain
  Demyelinating disease
  Parkinson's disease This invention discloses these QTT-positive patients show remarkable response to antiviral agent. They could and should be treated promptly in order to prevent the latent state and being an infectious source.

Those described above are the embodiments to exemplify the present disclosure to enable the person skilled in the art to understand, make and use embodiments of the present disclosure. This description, however, is not intended to limit the scope of the present disclosure. Any equivalent modification and variation according to the spirit of the present disclosure is to be also included within the scope of the claims stated below.

The components, steps, features, benefits and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, benefits and advantages. These also include embodiments in which the components and/or steps are arranged and/or ordered differently.

In reading the present disclosure, one skilled in the art will appreciate that embodiments of the present disclosure can be implemented in hardware, software, firmware, or any combinations of such, and over one or more networks. Suitable software can include computer-readable or machine-readable instructions for performing methods and techniques (and portions thereof) of designing and/or controlling the fabrication and design of integrated circuit chips according to the present disclosure. Any suitable software language (machine-dependent or machine-independent) may be utilized.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. The scope of protection is limited solely by the claims. That scope is intended and should be interpreted to be as broad as is consistent with the ordinary meaning of the language that is used in the claims when interpreted in light of this specification and the prosecution history that follows and to encompass all structural and functional equivalents.

Methods to detect the level of the specific immunoglobin E (IgE) to herpes simplex virus (HSV), vareicella zoster virus (VZV) antibodys in blood to diagnose, follow up and study the pathophysiology of the patients with blood high IgE (atopy) and mucocutaneous human herpesvirus (HHV) infections are necessary according to the following experience.

Atopy is a personal or familial tendency to produce IgE Ab in response to low doses of allergens, usually proteins, and to develop typical symptoms such as asthma, rhinoconjunctivitis, or dermatitis. Because the allergens which are well documented are difficult-to-avoid airborne and food allergens, the treatment for atopic dermatitis is still not satisfactory. There are more than one hundred sorts of specific IgE antibodies to these allergens were developed. However, they cannot reflect the clinical severity of atopy satisfactorily, thus cannot be used in the diagnosis and follow up of the atopy.

Diagnosis of the Patients

A one-step, two-minute cytological microscopic Quick Tzanck test (QTT) was used to diagnosis and follow-up patients with atopic dermatitis and mucocutaneous human herpesvirus (HHV) infections. QTTs of the vesicles, vesicopapules, pustules, erosions, and scales of the skin lesions were evaluated to determine the necessity of the antiviral agent.

Treatment of the Patients

Two antiviral agents, valacyclovir (500 mg) and acyclovir (200 mg), were prescribed based on the result of the QTT. Anti-allergic agents and topical corticosteroids (TCS) were also prescribed to treat the HHV-associated dermatitis. Serum total (nonspecific) and specific IgE for the environmental allergans, and HHV IgG (HSV, CMV and HVZ) antibodies EIA titer were evaluated in the same laboratory to study the correlation of the clinical improvement and the IgE level.

Discussion of the Result:

| | Date of Visit | | IgE-1 Total <170 U/mL | Cell Count WBC M 3900~9700 F 3500~9100/ mm³ | Cell Count Item EOSINO 1.0~5.0 (%) | CRP CRP <0.4 mg/dL*<0.3 mg/dL | IgG-1 HSV <2.0 | IgG-2 CMV <2.0 | IgG-3 HZV <2.0 |
|---|---|---|---|---|---|---|---|---|---|
| 1 | 1998 Aug. 5 | S01-V1 | 3165 | 7600 | 5.2 | 0.1* | | | |
| | 2008 Nov. 1 | S01-V2 | 19020 | 7200 | 10.6 | 0.39 | <2.0 | 26 | |
| | 2015 Sep. 11 | S01-V3 | 8713 | 7700 | 9.2 | 0.15 | <2.0 | 29.2 | |
| 2 | 2014 Feb. 5 | S02-V1 | 17930 | 14400 | 20 | 12.45 | <2.0 | | |
| | 2014 Feb. 28 | S02-V2 | 16773 | 8800 | 14.6 | 3.97 | | | |
| | 2015 Jan. 14 | S02-V3 | 14845 | 5400 | 16.1 | 0.05 | <2.0 | 50.3 | |
| | 2015 Mar. 18 | S02-V4 | 6064 | 5900 | 11.3 | <0.03 | | | |
| 3 | 2012 Sep. 7 | S03-V1 | 27012 | 7400 | 7.3 | <0.03 | <2.0 | <2.0 | |
| | 2015 May 29 | S03-V2 | 11550 | 7000 | 4.7 | 0.03 | <2.0 | <2.0 | |
| 4 | 1995 Dec. 25 | S04-V1 | 9934 | | | | | | |
| | 2011 Nov. 5 | S04-V2 | 32110 | 6800 | 7 | 0.60 | <2.0 | <2.0 | |
| | 2014 Mar. 26 | S04-V3 | 21020 | 7600 | 8 | 0.39 | <2.0 | | |
| 5 | 2011 Dec. 5 | S05-V1 | 3491 | | | | | | |
| | 2012 Jan. 6 | S05-V2 | 6122 | 6000 | 17.3 | 0.01 | 47.4 | 11.1 | |
| | 2012 Feb. 18 | S05-V3 | 6740 | 5800 | 5.4 | 0.01 | 28.3 | | |
| | 2017 Mar. 27 | S05-V4 | 1154 | 7200 | 6.1 | 0.08 | 38.6 | | 127.6 |
| 6 | 2010 Sep. 7 | S06-V1 | 17220 | 4600 | 9.7 | 0.05 | 78.4 | 9.3 | |
| | 2011 Dec. 12 | S06-V2 | 10650 | 6200 | 7.9 | 0.11 | 87.2 | 10.1 | |
| | 2013 Apr. 9 | S06-V3 | 4485 | 4600 | 14.4 | 0.20 | 128 | | |
| | 2016 Jan. 8 | S06-V4 | 2078 | 7400 | 7.6 | 0.05 | 67.1 | | |
| | 2017 Jan. 24 | S06-V5 | 2556 | 3900 | 7.4 | 0.45 | 72.2 | | 32.1 |
| 7 | 2009 Oct. 10 | S07-V1 | 10780 | 5900 | 5.1 | 0.04 | 103 | 4.7 | |
| | 2010 Nov. 15 | S07-V2 | 19460 | 5600 | 6.4 | 0.26 | >128 | | |
| | 2012 Nov. 7 | S07-V3 | 25156 | 7300 | 6.7 | 0.79 | 108 | | |
| | 2013 Nov. 6 | S07-V4 | 23287 | 6100 | 3.5 | 0.18 | >128 | | |
| | 2014 Dec. 12 | S07-V5 | 7100 | 6300 | 2.4 | 0.33 | >128 | | |
| | 2017 Jun. 14 | S07-V6 | 2322 | 5500 | 2.2 | 0.05 | >128 | | 5.3 |
| 8 | 2015 Mar. 25 | S08-V1 | 42542 | 14700 | 21 | 0.59 | 115 | | |
| | 2015 May 1 | S08-V2 | 38208 | 6000 | 11.1 | 0.06 | 103 | | |
| 9 | 2015 Nov. 2 | S09-V1 | 236 | 11400 | 1.1 | 1.06 | <2.0 | 8.6 | |
| | 2015 Nov. 21 | S09-V2 | 198 | 6400 | 2 | 0.03 | | | | patient 1: male, first visit: 15 Y/O
During the 15 years treated with Anti-allergic agents and TCS only, IgE increase from 3165 to 19020. The antiviral agent started on 2008 Sep. 13. The IgE decreased to 8713 after 6 years 10 months.

Patient 2: male, first visit: 15 Y/O
IgE decreased from 17930 to 6064 in 1 year and 1 month during antiviral agents.

Patient 3: male, first visit: 28 Y/O
IgE decreased from 27012 to 11550 in 2 year 8 months during antiviral agents.

Patient 4: male, first visit: 29 Y/O
During the 16 years treated with Anti-allergic agents and TCS only, IgE increase from 9934 to 32110. The antiviral agent started on 2011 May 9. The IgE decreased to 21020 in one year 4 months.

Patient 5: female, first visit: 14 Y/O
The IgE was 3491 when she was treated with oral steroid and TCS in other clinic. Even through the antiviral agent started on 2011 Dec. 27, the IgE increased to 6122 then to 6740 in 2 months. As the antiviral agent continued the IgE decreased to 1154 in 5 years 1 month.

Patient 6: male, first visit: 36 Y/O
The IgE was 17220 after one month of the antiviral agent. As the antiviral agent continued the IgE decreased to 2556 in 6 years 4 months.

Patient 7: male, first visit: 16 Y/O
The IgE was 5140 when he first visit my clinic in July 1998. Even through the antiviral agent started on 2008 Oct. 22, the IgE one year later was 10780. As the antiviral agent continued the IgE decreased to 2322 in 7 years 8 month.

Patient 8: male, first visit: 89 Y/O
He first visit my clinic due to severe whole body dermatitis. Two days after the valacyclovia 500 mg, twice a day the IgE was 42542. As the antiviral agent continued by valacyclovia 500 mg, once a day, IgE decreased to 38208 one month later.

Patient 9: female, first visit: 19 Y/O
She suffered from itchy papules over her back and hip for three months. The antiviral agent started on 2015 Oct. 19. The IgE was 236 after 2 weeks and decreased to 198 one month after the antiviral agent.

Even though the titer of the specific antibodys to many airborne and food allergens are available, as shown in the following table. The sum of these antibodys are quite small compared to the total (nonspecific) IgE level and nearly no change of the checked specific antibodys during the total IgE decreased from 19020 to 8713 in patients one. It's reasonable to suspect that the specific antibodys lessened by the antiviral agents are not included in the laboratory check of my patients.

| | | Class | | | | | | | |
|---|---|---|---|---|---|---|---|---|---|
| | | Cell Count | Cell Count | CRP | IgG-1 | IgG-2 | IgG-3 | IgE-1 | IgE-2 |
| | | | | | Item | | | | |
| Date of Visit | Normal Range | WBC M 3900~9700 F 3500~9100/ mm3 | EOSINO 1.0~5.0 (%) | CRP <0.4 mg/dL*<0.3 mg/dL | HSV <2.0 | CMV <2.0 | HZV | Total Non-specific IgE <170 U/mL | HD1 0~1: <0.69 2~6: >0.70, (UA/m) |
| 1998 Aug. 5 | S01-V1 | 7600 | 5.2 | 0.1* | | | | 3165 | |
| 2008 Nov. 1 | S01-V2 | 7200 | 10.6 | 0.39 | <2.0 | 26 | | 19020 | >100 |
| 2015 Sep. 11 | S01-V3 | 7700 | 9.2 | 0.15 | <2.0 | 29.2 | | 8713 | >100 |
| 2014 Feb. 5 | S02-V1 | 14400 | 20 | 12.45 | <2.0 | | | 17930 | |
| 2014 Feb. 28 | S02-V2 | 8800 | 14.6 | 3.97 | | | | 16773 | |
| 2015 Jan. 14 | S02-V3 | 5400 | 16.1 | 0.05 | <2.0 | 50.3 | | 14845 | |
| 2015 Mar. 18 | S02-V4 | 5900 | 11.3 | <0.03 | | | | 6064 | |
| 2012 Sep. 7 | S03-V1 | 7400 | 7.3 | <0.03 | <2.0 | <2.0 | | 27012 | |
| 2015 May 29 | S03-V2 | 7000 | 4.7 | 0.03 | <2.0 | <2.0 | | 11550 | |
| 1995 Dec. 25 | S04-V1 | | | | | | | 9934 | >100 |
| 2011 Nov. 5 | S04-V2 | 6800 | 7 | 0.60 | <2.0 | <2.0 | | 32110 | >100 |
| 2014 Mar. 26 | S04-V3 | 7600 | 8 | 0.39 | <2.0 | | | 21020 | |
| 2011 Dec. 5 | S05-V1 | | | | | | | 3941 | 72.2 |
| 2012 Jan. 6 | S05-V2 | 6000 | 17.3 | 0.01 | 47.4 | 11.1 | | 6122 | |
| 2012 Feb. 18 | S05-V3 | 5800 | 5.4 | 0.01 | 28.3 | | | 6740 | |
| 2017 Mar. 27 | S05-V4 | 7200 | 6.1 | 0.08 | 38.6 | | | 1154 | |
| 2010 Sep. 7 | S06-V1 | 4600 | 9.7 | 0.05 | 78.4 | 9.3 | | 17220 | >100 |
| 2011 Oct. 12 | S06-V2 | 6200 | 7.9 | 0.11 | 87.2 | 10.1 | | 10650 | >100 |
| 2013 Apr. 9 | S06-V3 | 4600 | 14.4 | 0.20 | 128 | | | 4485 | |
| 2016 Jan. 8 | S06-V4 | 7400 | 7.6 | 0.05 | 67.1 | | | 2078 | 96.1 |
| 2017 Jan. 24 | S06-V5 | 3900 | 7.4 | 0.45 | | | | 2556 | 86.5 |
| 2009 Oct. 10 | S07-V1 | 5900 | 5.1 | 0.04 | 103 | 4.7 | | 10780 | |
| 2010 Nov. 15 | S07-V2 | 5600 | 6.4 | 0.26 | >128 | | | 19460 | |
| 2012 Nov. 7 | S07-V3 | 7300 | 6.7 | 0.79 | 108 | | | 25156 | |
| 2013 Nov. 6 | S07-V4 | 6100 | 3.5 | 0.18 | >128 | | | 23287 | |
| 2014 Dec. 12 | S07-V5 | 6300 | 2.4 | 0.33 | >128 | | | 7100 | |
| 2017 Jun. 14 | S07-V6 | 5500 | 2.2 | 0.05 | >128 | | | 2322 | 82.6 |
| 2015 Mar. 25 | S08-V1 | 14700 | 21 | 0.59 | 115 | | | 43542 | 0.52 |
| 2015 May 1 | S08-V2 | 6000 | 11.1 | 0.06 | 103 | | | 38208 | |
| 2015 Nov. 2 | S09-V1 | 11400 | 1.1 | 1.06 | <2.0 | 8.6 | | 236 | 11.3 |
| 2015 Nov. 21 | S09-V2 | 6400 | 2 | 0.03 | | | | 198 | |

| | Class | | | | | | | |
|---|---|---|---|---|---|---|---|---|
| | IgE-3 | IgE-4 | IgE-5 | IgE-6 | IgE-7 | IgE-8 | IgE-9 | IgE-10 |
| | | | | Item | | | | |
| Date of Visit | SEB | Fungus C: *Cladosporium* | Cedar | 動物皮 AS屑 0~1: <0.69 2~6: >0.70, (UA/m) | TMT Tomato | MG | Mites | *Candida* カンジダ |
| 1998 Aug. 5 | | | | | | | | |
| 2008 Nov. 1 | 1.74 | 13.9 | | | | | | |
| 2015 Sep. 11 | 1.78 | 3.57 | | | | | | |
| 2014 Feb. 5 | | | | | | | | |
| 2014 Feb. 28 | | | | | | | | |
| 2015 Jan. 14 | | | | | | | | |
| 2015 Mar. 18 | | | | | | | | |
| 2012 Sep. 7 | | | | | | | | |
| 2015 May 29 | | | | | | | | |
| 1995 Dec. 25 | | <0.34[C] | | | | | >100 | <0.34 |
| 2011 Nov. 5 | 0.64 | 1.83 | 75.8 | | | | | |
| 2014 Mar. 26 | | | | | | | | |
| 2011 Dec. 5 | | | >100 5.13[h] | 0.82[d] | | | 89[a] | 89[a] |
| 2012 Jan. 6 | | | | | | | | |
| 2012 Feb. 18 | <0.34 | <0.34 | | | | 0.11[MF] | 39.2[b] | 39.2[b] |
| 2017 Mar. 27 | | | | | | | 10.9[b] | 10.9[b] |
| 2010 Sep. 7 | 1.13 | 16 | | | 15.7 | | | |
| 2011 Oct. 12 | 0.51 | 12.2 | >100 | | | 18.9 | | |
| 2013 Apr. 9 | | | | | | | | |
| 2016 Jan. 8 | | 3.14 | | | 1.87 | 11.3 | | |
| 2017 Jan. 24 | | | | | | | | |
| 2009 Oct. 10 | | | 54.4 | | | 46.80[MG] | | |

-continued

| | | | | 20.20$^{Mg}$ |
|---|---|---|---|---|
| 2010 Nov. 15 | | | | |
| 2012 Nov. 7 | | | | |
| 2013 Nov. 6 | | | | |
| 2014 Dec. 12 | | | | |
| 2017 Jun. 14 | | | 5.34 | |
| 2015 Mar. 25 | 70 | 4.55 | | |
| 2015 May 1 | | | | |
| 2015 Nov. 2 | 7.07 | <0.10 | | |
| 2015 Nov. 21 | | | | |

According to the guidelines for atopy, patients suffering from recurrent itching skin eruptions should be treated with Anti-allergic agents and TCS as I did for the patients 1 and 4. The IgE of patients 1 increased from 3165 to 19020 in 15 years and of patient 4 from 9934 to 32110 in 16 years. On the other hands, after the antiviral agent was added, the IgE of patient 1 decreased from 19020 to 8713 in 6 years 10 months and, the IgE of patient 4 decreased from 32110 to 21020 in one year 4 months. Not only the level of the total IgE decrease but also clinical improvement of the dermatitis were observed in all the patients studied. In summary, antiviral agents for HHV brought about the decrease of total IgE.

In order to diagnose, follow up and study the pathophysiology of the patients with blood high IgE (atopy) and mucocutaneous human herpesvirus (HHV) infections, methods to detect the level of the specific IgE antibodys to HSV, VZV antibodys and other HHV in blood are necessary.

Below are formula of some pharmaceutical composition those are useful in treating one suffering from human herpesvirus (HHV) associated dermatosis and non-dermatosis diseases, wherein the dermatosis include acnes, impetigo, pyoderma gangrenosum, chilblains and psoriasiform, asteatotic dermatitis, ichthylosis, lichen simplex chronics (Neurodermatitis, Prurigo), seborrheoeic dermatitis, rosacea, perioral dermatitis, epidermal cyst, wound ulcer, discoid lupus erythematosus, vitiligo, alopecia, diagnostic criteria of some autoimmune diseases such as systemic lupus erythematosus or diabetic skin complication, and wherein the non-dermatosis include glomerulonephritis, arthritis, Crohn's disease, ulcerative colitis, myelodysplasia, multiple myeloma, demyelinating disease, Parkinson's disease, anemia, cytopenia those among the diagnostic criteria.

The formula of the pharmaceutical composition for treating atopic dermatitis of a human that is induced by Herpes simplex virus (HSV) includes: For adults
1. Acyclovir 200 mg with Tranilast 100 mg Q 8 hours
2. Valacyclovir 500 mg with Fexofenadine hydrochloride 60 mg Q12 hours
3. Valacyclovir 500 mg with Mequitazine 3 mg Q12 hours
4. Alacyclovir 500 mg with Oropatadine hydrochloride 5 mg Q12 hours
5. Valacyclovir 500 mg with Epinastine hydrochloride 10 mg after dinner
6. Valacyclovir 500 mg with Loratadine 10 mg after dinner
7. Valacyclovir 500 mg with Cetirizine hydrochloride 10 mg after dinner
For child below 12 years old (body weight around 40 KG)
Acyclovir 200 mg with Tranilast Q 8 hours
For child below 7 years old (body weight below 20 KG)
Acyclovir syrup 15 mg/KG with Tranilast 2 mg/KG Q 8 hours
Acyclovir granule 15 mg/KG with Tranilast 2 mg/KG Q 8 hours Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A pharmaceutical composition for treating atopic dermatitis of a human that is induced by Herpes simplex virus (HSV), said pharmaceutical composition comprising an effective amount of 2-[(2-amino-6-oxo-6,9-dihydro-3H-purin-9-yl)methoxy]ethyl-2-amino-3-methylbutanoate and an effective amount of an Anti-allergic agent.

2. The pharmaceutical composition of claim 1, wherein said pharmaceutical composition comprises Valacyclovir 500 mg and Fexofenadine hydrochloride 60 mg.

3. The pharmaceutical composition of claim 1, wherein said pharmaceutical composition comprises Valacyclovir 500 mg and Mequitazine 3 mg.

4. The pharmaceutical composition of claim 1, wherein said pharmaceutical composition comprises Valacyclovir 500 mg and Epinastine hydrochloride 10 mg.

5. The pharmaceutical composition of claim 1, wherein said pharmaceutical composition comprises Valacyclovir 500 mg and Loratadine 10 mg.

6. The pharmaceutical composition of claim 1, wherein said pharmaceutical composition comprises Valacyclovir 500 mg and Cetirizine hydrochloride 10 mg.

7. A pharmaceutical composition for treating atopic dermatitis of a human that is induced by Herpes simplex virus (HSV), said pharmaceutical composition comprising an effective amount of 2-Amino-1,9-dihydro-9-((2-hydroxyethoxy)methyl)-6H-purin-6-one and an effective amount of an Anti-allergic agent.

8. The pharmaceutical composition of claim 7, wherein said pharmaceutical composition comprises Acyclovir 200 mg and Tranilast 100 mg.

9. The pharmaceutical composition of claim 7, wherein said pharmaceutical composition comprises Acyclovir 500 mg and Oropatadine hydrochloride 5 mg.

* * * * *